United States Patent
Role

(10) Patent No.: US 6,284,535 B1
(45) Date of Patent: *Sep. 4, 2001

(54) SPLICE VARIANTS OF THE HEREGULIN GENE, NARIA AND USES THEREOF

(75) Inventor: Lorna W. Role, New York, NY (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/697,954

(22) Filed: Sep. 4, 1996

Related U.S. Application Data

(60) Provisional application No. 60/003,380, filed on Sep. 7, 1995.

(51) Int. Cl.$^7$ .............................. C12N 5/00; C12P 21/06; C07H 17/00; C07K 14/00
(52) U.S. Cl. ................... 435/325; 435/69.1; 435/320.1; 435/252.3; 536/23.1; 530/350
(58) Field of Search ................................. 330/350; 514/2; 435/69.1, 326.1, 325, 252.3; 536/23.1; 530/350

(56) References Cited

PUBLICATIONS

Chu, G.C. et al., (1995) Regulation of the acetylcholine receptor and subunit gene by recombinant ARIA: an in vitro model for transynaptic gene regulation. Neuron 14:329–339 (Exhibit 2).
Corfas, G. et al., (1995) Differential expression of ARIA isoforms in the rat brain. Neuron 14:103–115 (Exhibit 3).
Fall, D.L. et al., (1993) ARIA, a protein that stimulates acetylcholine receptor synthesis, is a member of the neu ligand family. Cell 72:801–815 (Exhibit 4).
Ho, W–H, et al., (1995) Sensory and motor neuron–derived factor. J. of Biol Chem. 270(24):14523–14532 (Exhibit 5).
Holmes, W.E. et al., (1992) Identification of heregulin, a specific activator of p185erbB2. Science 256:1205–1210 (Exhibit 6).
Kuo, Y. et al., (1994) Isolation and characterization of chick and human nARIA, a novel member of the ERBB2/HER ligand family which lacks the immunoglobin domain. Soc. for Neurosc. Abstr. 20:1095 (Exhibit 7).
Kuo, Y. et al., (1993) Expression of members of the neu (ARIA)ligand family in chick and rat central nervous system. Soc. for Neurosc. Abstr. 19:1725 (Exhibit 8).
McGehee, D.S. et al., (1995) Nicotine enhancement of fast excitatory synaptic transmission in CNS by presynaptic receptors. Science 269:1692–1696 (Exhibit 9).
Mudge, A.W. et al., (1993) New ligands for neu? Current Biol. 3(6):361–364 (Exhibit 10).
Sivilotti, L. and Colquhon, D. (1995) Acetylcholine receptors: too few functions. Science 269:1681–1682 (Exhibit 11).
Vartanian, T. et al., (1994) A role for the acetylcholine receptor–inducing protein ARIA in oligodendrocyte development. PNAS, U.S.A. 91–11626–11630 (Exhibit 12).
Wen, D. et al., (1992) Neu differentiation factor: a transmembrane glycoprotein containing an EGF Domain and an immunoglobulin homology unit. Cell 69:559–572 (Exhibit 13). and.
Yang, X. et al., (1994) Identification of different ARIA splice variants expressed by chick cns and pns neurons during development. Soc. for the Neurosc. Abstr. 20:1095 (Exhibit 14).

*Primary Examiner*—Karen Cochrane Carlson
(74) *Attorney, Agent, or Firm*—John P. White; Cooper & Dunham LLP

(57) ABSTRACT

This invention provides an isolated nucleic acid molecule encoding an nARIA polypeptide, including human nARIA (hnARIA) and chicken nARIA (cnARIA). These nucleic acid molecules may be DNA, cDNA, or RNA. This invention also provides for a purified nARIA polypeptide. This invention provides for a replicable vector comprising an nARIA sequence and host cells comprising this vector. This invention provides for a composition comprising the nARIA polypeptide and a pharmaceutically acceptable carrier. One embodiment of this invention is a method for inducing the formation of a synaptic junction between a neuron and a target cell comprising contacting the target cell with an nARIA polypeptide or a nucleic acid molecule encoding nARIA in an amount sufficient to induce the formation of a synaptic junction.

15 Claims, 25 Drawing Sheets

FIGURE 1A

```
   1  CGGATGCTGC TGCTACTGTC ACTTCTGCCG CTGCCGCTGT TGTTACAGAT
  51  TTTGCTTTTG CTCCTTCTAC CGCATGACAA TTGTTTTCCT CGCCTAAGCA
 101  GATACCAGCC TCAGATGCTC AAGGTGAGAG TCTTGCCTTT CGCTCTGGGC
 151  TATTGGTTCA CTTAATCCGG TCAATTTGTT CGCTGCTCGT GGTTGTCTTT
 201  CTCCCCGCCC TCCTTCCCCC TGTTTTGTTT TGTTTCGCTT GCTTTCGGGG
 251  GGACGCTCCT TCCCTCAGTC AGAAGAGCTG GAATTGCTTG AGAGGCGTAT
 301  AAGGAATTAT AAAAGTGGCC AGGAAACACG AGCGCAGTGA CTGCAGAGCT
 351  GCCCTTGGCT TCGGCAAGGC AGCGTGAGCG GCAGAGGGCT CGGGCAGGGG
 401  GCGGGGGGTC TCCTTTTTCC CGTGCGTTCC TCTTCTCCCA GTTCGGATGA
 451  TGTTGCTGTT TCGGACCTCT CGCTGACTCC TGCCCTGTGA TTTTTGCTGA
 501  GCGCTGTGAC TGTTACTCCG TCTCTTTCTG TCTGTGTTTC ACAGTAATGG
 551  ACTGTGATAG AGTTAAGGCC TTTTGGAGGT GAGCTGTGTC ACAGCTGATG
 601  CTTAAACATG TCTGAAGTAG GCACCGAGAC TTTCCCCAGC CCCTCGGCTC
 651  AGCTGAGCCC TGATGCATCC CTTGGCGGGC TCCCGGCTGA GGAGAACATG
 701  CCGGGGCCCC ACAGAGAGGA CAGCAGGGTC CCAGGTGTGG CAGGCCTGGC
 751  CTCGACCTGC TGCGTGTGCC TGGAAGCAGA GCGACTGAAG GGCTGCCTCA
 801  ACTCTGAGAA GATCTGCATC GCCCCTATCC TGGCTTGCCT GCTCAGCCTC
 851  TGCCTCTGCA TTGCTGGCCT CAAGTGGGTC TTTGTGGACA AGATTTTTGA
 901  GTATGACTCT CCTACACACC TTGACCCTGG GAGGATAGGA CAAGACCCAA
 951  GGAGCACTGT GGATCCTACA GCTCTGTCTG CCTGGGTGCC TTCGGAGGTG
1001  TATGCCTCAC CCTTCCCCAT ACCTAGCCTT GAGAGCAAGG CTGAAGTGAC
1051  AGTGCAAACT GACAGCTCGC TCGTGCCCTC AGGCCCTTC CTTCAGCCTT
1101  CTCTCTACAA CCGCATCCTA GATGTCGGGT TGTGGTCCTC TGCCACACCG
1151  TCACTGTCAC CATCCTCCCT GGAGCCTACC ACGGCATCTC AGGCACAAGC
1201  AACAGAAACC AATCTCCAAA CTGCTCCAAA ACTTTCCACT TCTACATCTA
1251  CAACTGGGAC AAGTCATCTC ACAAAATGTG ACATAAAGCA GAAAGCCTTC
1301  TGTGTAAATG GGGAGAGTG CTACATGGTT AAAGACCTCC CAAACCCTCC
```

FIGURE 1B

```
1351  ACGATACCTA TGCAGGTGCC CAAATGAATT TACTGGTGAT CGCTGCCAAA
1401  ACTACGTAAT GGCCAGCTTC TACAAGCATC TTGGGATTGA ATTTATGGAA
1451  GCTGAGGAAC TGTACCAGAA ACGGGTGCTG ACCATAACTG GCATTTGCAT
1501  TGCTCTTCTA GTAGTTGGCA TCATGTGTGT GGTGGCCTAC TGCAAAACCA
1551  AGAAGCAGAG GAAAAGTTG CATGACCGCC TTCGGCAGAG CCTTCGCTCA
1601  GAGAGGAACA ACGTTATGAA CATGGCAAAT GGGCCACACC ACCCCAACCC
1651  ACCACCAGAC AATGTCCAGC TGGTGAATCA GTACGTTTCA AAAACATAA
1701  TCTCCAGTGA ACGTGTCGTT GAGCGAGAAA CCGAGACCTC GTTTTCCACA
1751  AGCCACTACA CCTCAACAAC TCATCACTCC ATGACAGTCA CCCAGACGCC
1801  TAGCCACAGC TGGAGTAATG GCCATACCGA AGCATTCTC TCCGAAAGCC
1851  ACTCCGTGCT CGTCAGCTCC TCAGTGGAGA ATAGCAGGCA CACCAGCCCA
1901  ACAGGGCCAC GAGGCCGCCT CAATGGCATT GGTGGGCCAA GGGAAGGCAA
1951  CAGCTTCCTC CGGCATGCAA GAGAGACCCC TGACTCCTAC CGAGACTCTC
2001  CTCACAGTGA AAGGTATGTC TCAGCTATGA CCACACCAGC TCGCATGTCA
2051  CCCGTTGATT TCCACACTCC AACTTCTCCC AAGTCCCTC CATCTGAAAT
2101  GTCACCACCA GTTTCCAGCT TGACCATCTC CATCCCTTCG GTGGCGGTGA
2151  GTCCCTTTAT GGACGAGGAG AGACCGCTGC TGTTGGTGAC CCCACCACGG
2201  CTGCGTGAGA AGTACGACAA CCACCTTCAG CAATTCAACT CCTTCCACAA
2251  CAATCCCACC CATGAGAGCA ACAGTCTGCC ACCCAGTCCT CTGAGGATAG
2301  TGGAGGATGA AGAGTATGAG ACCACGCAGG AGTACGAACC AGCACAGGAG
2351  CCTCCAAAGA AACTCACCAA CAGCCGGAGG GTGAAAAGAA CAAAGCCCAA
2401  TGGCCATATT TCCAGCAGGG TAGAAGTGGA CTCCGACACA AGCTCTCAGA
2451  GCACTAGCTC TGAGAGCGAA ACAGAAGATG AAAGAATAGG TGAGGATACA
2501  CCATTTCTTA GCATACAAAA TCCCATGGCA ACCAGTCTGG AGCCAGCCGC
2551  TGCATATCGG CTGGCTGAGA ACAGGACTAA CCCGGCAAAT CGCTTCTCCA
2601  CACCAGAAGA GTTGCAAGCA AGGTTGTCCA GTGTAATAGC TAACCAAGAC
2651  CCTATTGCTG TATAAGACAT AAACAAAACA CATAGATTCA CATGTAAAAC
```

FIGURE 1C

```
2701  TTTATTTTAT ATAATGAAGT ATTCCACCTT TAAATTAAAC AATTTATTTT
2751  ATTTTAGCAA TTCCGCTGAT AGAAAACAAG AGTGGAAAAA GAAACTTTTA
2801  TAAATTAAGT ATACGTATGT ACAAATGTGT TATGTGCCAT ATGTAGCAAT
2851  TTTTTACAGT ATTTCCAAAA TGGGGAAAGA TATCAATGGT GCCTTTATGT
2901  TATGTTATGT TGAGAGCAAG TTTTGTACAG CTACAATGAT TGCTGTCCCG
2951  TAGTATTTTG CAAAACCTTC TAGCCCTCAG TTGTTCTGGC TTTTTTGTGC
3001  ATTGCATTAT AATGACTGGA TGTATGATTT GCAAGAATTG CAGAAGTCCC
3051  CATTTGCTTG TTGTGGAATC CCCAGATCAA AAGCCCTGT TATGGCACTC
3101  ACACCCTATC CACTTCACCA GGAAAAAAAA AAAATCAAAA AAAAAAAAA
3151  AAAAAAAGA AAAGAAAGAG AAAAAGAAA AGAAAAGAA AAAAAAGCT
3201  GAAAAAATAA AA
```

FIGURE 2

```
   1  GCCCYCHFCR CRCCYRFCFC SFYRMTIVFL A*ADTSLRCS R*ESCLSLWA
  51  IGSLNPVNLF AARGCLSPRP PSPCFVLFRL LSGGRSFPQS EELELLERRI
 101  RNYKSGQETR AQ*LQSCPWL RQGSVSGRGL GQGAGGLLFP VRSSSPSSDD
 151  VAVSDLSLTP AL*FLLSAVT VTPSLSVCVS Q*WTVIELRP FGGELCHS*C
 201  LNMSEVGTET FPSPSAQLSP DASLGGLPAE ENMPGPHRED SRVPGVAGLA
 251  STCCVCLEAE RLKGCLNSEK ICIAPILACL LSLCLCIAGL KWVFVDKIFE
 301  YDSPTHLDPG RIGQDPRSTV DPTALSAWVP SEVYASPFPI PSLESKAEVT
 351  VQTDSSLVPS RPFLQPSLYN RILDVGLWSS ATPSLSPSSL EPTTASQAQA
 401  TETNLQTAPK LSTSTSTTGT SHLTKCDIKQ KAFCVNGGEC YMVKDLPNPP
 451  RYLCRCPNEF TGDRCQNYVM ASFYKHLGIE FMEAEELYQK RVLTITGICI
 501  ALLVVGIMCV VAYCKTKKQR KKLHDRLRQS LRSERNNVMN MANGPHHPNP
 551  PPDNVQLVNQ YVSKNIISSE RVVERETETS FSTSHYTSTT HHSMTVTQTP
 601  SHSWSNGHTE SILSESHSVL VSSSVENSRH TSPTGPRGRL NGIGGPREGN
 651  SFLRHARETP DSYRDSPHSE RYVSAMTTPA RMSPVDFHTP TSPKSPPSEM
 701  SPPVSSLTIS IPSVAVSPFM DEERPLLLVT PPRLREKYDN HLQQFNSFHN
 751  NPTHESNSLP PSPLRIVEDE EYETTQEYEP AQEPPKKLTN SRRVKRTKPN
 801  GHISSRVEVD SDTSSQSTSS ESETEDERIG EDTPFLSIQN PMATSLEPAA
 851  AYRLAENRTN PANRFSTPEE LQARLSSVIA NQDFIAV*DI NKTHRFTCKT
 901  LFYIMKYSTF KLNNLFYFSN SADRKQEWKK KLL*IKYTYV QMCYVPYVAI
 951  FYSISKMGKD INGAFMLCYV ESKFCTATMI AVP*YFAKPS SPQLFWLFCA
1001  LHYNDWMYDL QELQKSPFAC CGIPRSKSPV MALTPYPLHQ EKKKIKKKKK
1051  KKRKEREKRK EKEKKS*KNK
```

FIGURE 3

```
   1  CGGCCTGTAA GATGCTGTAT CATTTGGTTG GGGGGGCCTC TGCGTGGTAA
  51  TGGACCGTGA GAGCGGCCAG GCCTTCTTCT GGAGGTGAGC CGATGGAGAT
 101  TTATTCCCCA GACATGTCTG AGGTCGCCGC CGAGAGGTCC TCCAGCCCCT
 151  CCACTCAGCT GAGTGCAGAC CCATCTCTTG ATGGGCTTCC GGCAGCAGAA
 201  GACATGCCAG AGCCCCAGAC TGAAGATGGG AGAACCCCTG GACTCGTGGG
 251  CCTGGCCGTG CCCTGCTGTG CGTGCCTAGA AGCTGAGCGC CTGAGAGGTT
 301  GCCTCAACTC AGAGAAAATC TGCATTGTCC CCATCCTGGC TTGCCTGGTC
 351  AGCCTCTGCC TCTGCATCGC CGGCCTCAAG TGGGTATTTG TGGACAAGAT
 401  CTTTGAATAT GACTCTCCTA CTCACCTTGA CCCTGGGGGG TTAGGCCAGG
 451  ACCCTATTAT TTCTCTGGAC GCAACTGCTG CCTCAGCTGT GTGGGTGTCG
 501  TCTGAGGCAT ACACTTCACC TGTCTCTAGG GCTCAATCTG AAAGTGAGGT
 551  TCAAGTTACA GTGCAAGGTG ACAAGGCTGT TGTCTCCTTT GAACCATCAG
 601  CGGCACCGAC ACCGAAGAAT CGTATTTTTG CCTTTTCTTT CTTGCCGTCC
 651  ACTGCGCCAT CCTTCCCTTC ACCCACCCGG AACCCTGAGG TGAGAACGCC
 701  CAAGTCAGCA ACTCAGCCAC AAACAACAGA AACTAATCTC CAAACTGCTC
 751  CTAAACTTTC TACATCTACA TCCACCACTG GACAAGCCA TCTTGTAAAA
 801  TGTGCGGAGA AGGAGAAAAC TTTCTGTGTG AATGGAGGGG AGTGCTTCAT
 851  GGTGAAAGAC CTTTCAAACC CCTCGAGATA CTTGTGCAAA GGCGGAGGAG
 901  CTGTACCAGA AGAGAGTGCT GACCATAACC GGCATCTGCA TCGCCCTCCT
 951  TGTGGTCGGC ATCATGTGTG TGGTGGCCTA CTGCAAAACC AAGAAACAGC
1001  GGAAAAAGCT GCATGACCGT CTTCGGCAGA GCCTTCGGTC TGAACGAAAC
1051  AATACGATGA ACATTGCCAA TGGGCCTCAC CATCCTAACC CACCCCCCGA
1101  GAATGTCCAG CTGGTGAATC AATACGTATC TAAAAACGTC ATCTCCAGTG
1151  AGCATATTGT TGAGAGAGAA GCAGAGACAT CCTTTTCCAC CAGTCACTAT
1201  ACTTCCACAG CCCATCACTC CACTACTGTC ACCCAGACTC CTAGCCACAG
1251  CTGGAGCAAC GGACACACTG AAAGCATCCT TTCCGAAAGC CACTCTGTAA
1301  TCGTGATGTC ATCCGTAGAA AACAGTAGGC ACAGCAGCCC AACTGGGGCC
1351  G
```

FIGURE 4

```
  1   ACKMLYHLVG  GASAW*WTVR  AARPSSGGEP  MEIYSPDMSE  VAAERSSSPS
 51   TQLSADPSLD  GLPAAEDMPE  PQTEDGRTPG  LVGLAVPCCA  CLEAERLRGC
101   LNSEKICIVP  ILACLVSLCL  CIAGLKWVFV  DKIFEYDSPT  HLDPGGLGQD
151   PIISLDATAA  SAVWVSSEAY  TSPVSRAQSE  SEVQVTVQGD  KAVVSFEPSA
201   APTPKNRIFA  FSFLPSTAPS  FPSPTRNPEV  RTPKSATQPQ  TTETNLQTAP
251   KLSTSTSTTG  TSHLVKCAEK  EKTFCVNGGE  CFMVKDLSNP  SRYLCKGGGA
301   VPEESADHNR  HLHRPPCGRH  HVCGGLLQNQ  ETAEKAA*PS  SAEPSV*TKQ
351   YDEHCQWASP  S*PTPRECPA  GESIRI*KRH  LQ*AYC*ERS  RDILFHQSLY
401   FHSPSLHYCH  PDS*PQLEQR  TH*KHPFRKP  LCNRDVIRRK  Q*AQQPNWG
```

ED5 trunk cross-section nARIA specific probe

ED5 trunk cross-section

ARIA specific probe nARIA specific probe

ED7 trunk cross-section

ARIA specific probe

ED7 trunk cross-section

FIGURE 11A FIGURE 11B
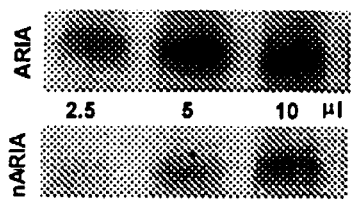
A. MCF-7
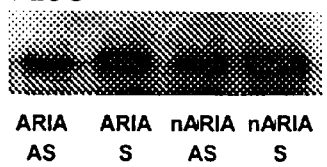
B. LSG
FIGURE 11C
C. TIME COURSE

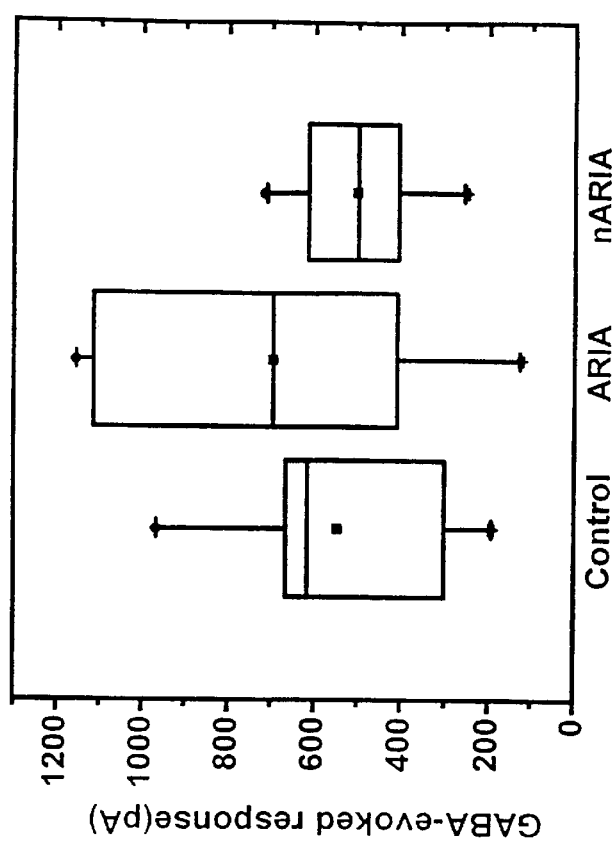
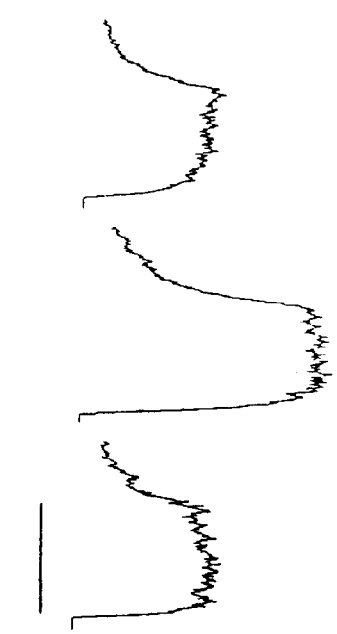
FIGURE 13D
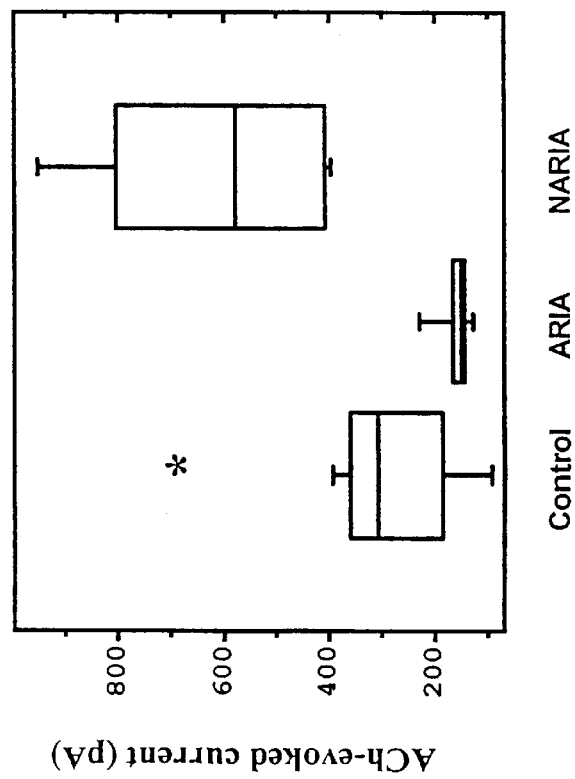
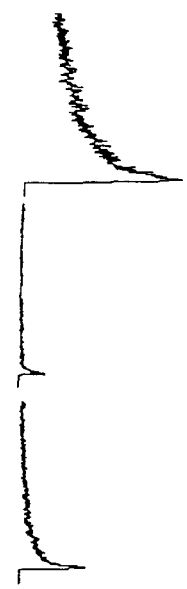
FIGURE 13C

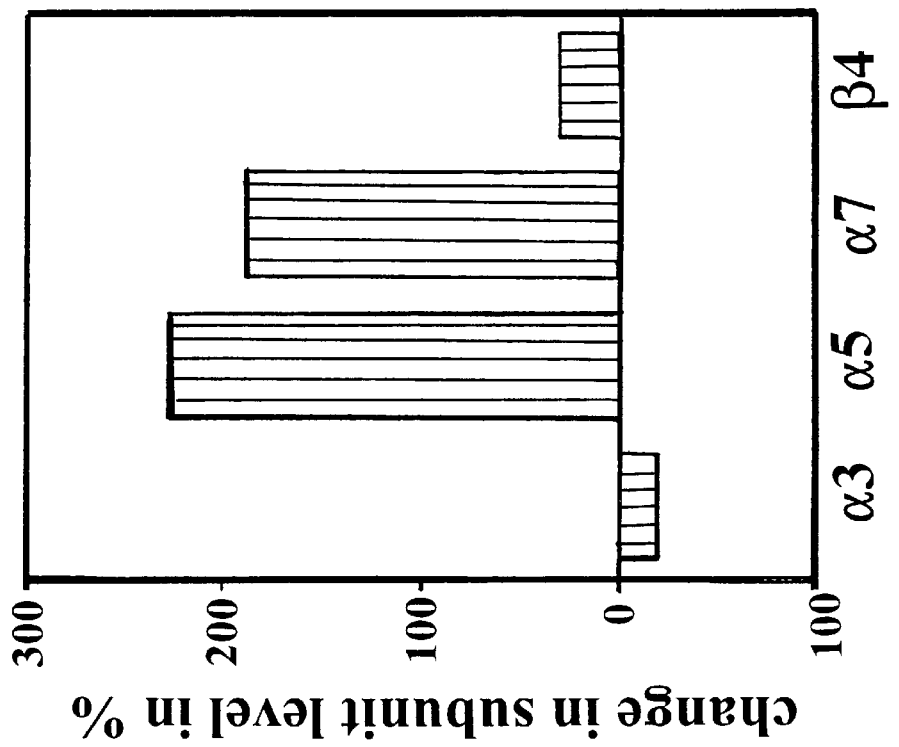
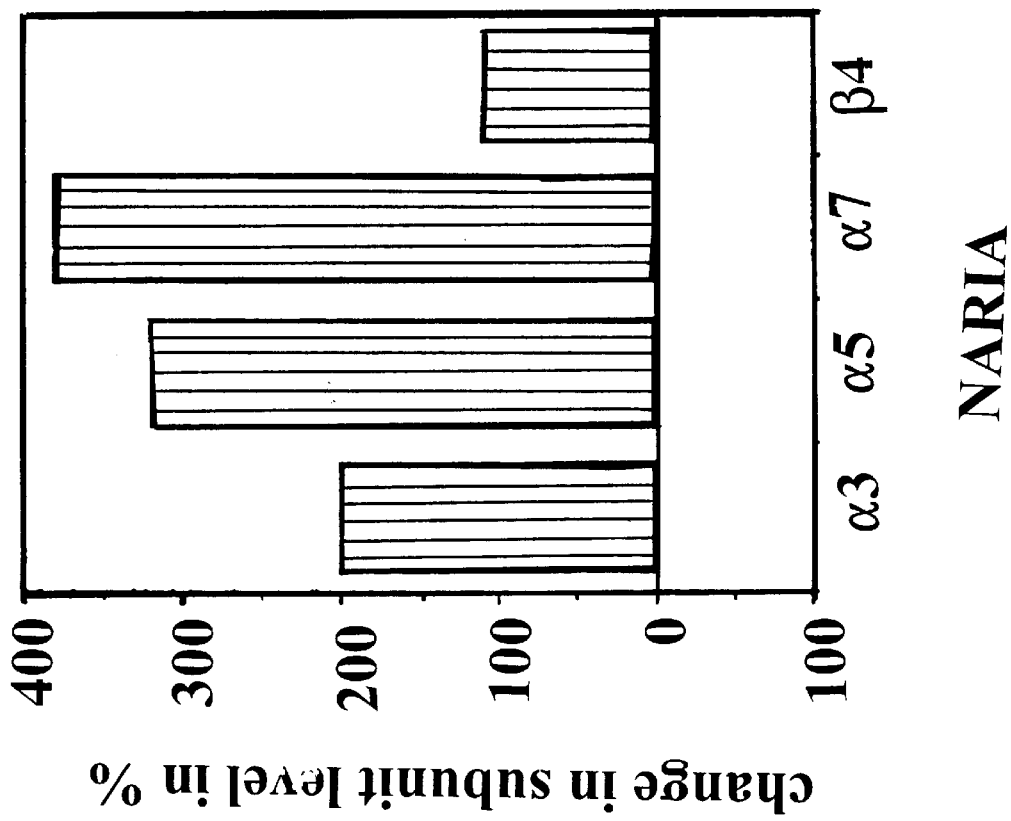
FIGURE 14A
FIGURE 14B no treatment=sympathetic neurons alone
'Pre'=treatment of sympathetic neurons with presynaptic input-conditioned media+various oligos
mmAS=mismatch antisense control
nARIA AS=nARIA specific antisense oligonucleotides
ARIA AS=ARIA specific antisense oligonucleotides

SPLICE VARIANTS OF THE HEREGULIN GENE, NARIA AND USES THEREOF

This application claims the benefit of U.S. Provisional Application No. 60/003,380, filed Sep. 7, 1995, the contents of which are hereby incorporated by reference into the present application.

A portion of the invention disclosed herein was made with Government support under NIH Grant No. NS29071 from the Department of Health and Human Services. Accordingly, the U.S. Government may have certain rights in this invention.

BACKGROUND OF THE INVENTION

Throughout this application, various publications are referenced by author and date. Full citations for these publications may be found listed alphabetically at the end of the specification immediately preceding the claims. The hereby incorporated by reference into this application in order to more fully describe the state of the art as known to those skilled therein as of the date of the invention described and claimed herein.

The development and differentiation of embryonic neurons culminates in synapse formation. Neuronal development is an intricate process that involves a cascade of inductive interactions between a neuron and the pre- and postsynaptic partners of that neuron. These highly regulated events are important for the establishment of reliable, yet plastic, synaptic formation and transmission. Correct expression of an array of transmitter-gated channels by neurons is clearly essential to synaptic differentiation, and yet the developmental regulation of this process is poorly understood. In fact, despite overwhelming advances in probing the molecular and biophysical details of ion channels gated by gamma-amino butyric acid (GABA), glycine, glutamate and acetylcholine (ACh) (Betz, 1990; Deneris et al., 1991; McGehee et al., 1995; Role, 1992; Sargent, 1993) the corresponding embryonic versions of these receptors have evaded analysis. Characterization of the biophysical properties of ligand-gated channels in developing neurons and description of their evolution to the mature receptor profile is limited (Brussard et al., 1994; Moss and Role, 1993; Margiotta and Gurantz, 1989). Furthermore, little is known about the mechanism of these changes.

The study of embryonic ligand-gated channels and subsequent modifications of their functional profile during neural development is difficult. Receptor expression prior to synaptogenesis is at a low level. Synapse formation is not synchronous. In the few cases studied, the developmental changes in receptor function are vast (Berg et al., 1989; Engisch and Fischbach, 1992; Arenella et al, 1993; Deneris et al, 1991; McGehee and Role, 1995; Role, 1992; Sargent, 1993). In the establishment of mature synapses, profound alterations in the expression profile of neuronal ligand-gated channels occur. In addition to these changes in expression levels, changes in the cellular distribution, the subunit composition and the biophysical and pharmacological properties occur as well (Margiotta and Gurantz, 1989; Moss and Role, 1993; Moss et al., 1989; Devay et al, 1994; Arenella et al, 1993; Jacob, 1991; Mandelzys et al, 1994; Smith et al, 1983; Vernallis et al, 1993). The interactions between presynaptic and target neurons may play a large role in the extrinsic influences which are believed to modify receptor function throughout development. The mechanism of receptor development remains unclear, however, presynaptic input, target cell regulation, synaptic activity or molecular signals independent of transmission may be involved.

Diversity of Neuronal Nicotinic Receptors

One important feature of neuronal ligand-gated channels, nicotinic acetylcholine receptors (nAChRs) in particular, is the diversity of component subunits and the resultant diversity in channel subtypes (Boulter et al, 1986; Conroy et al., 1992; Grynkiewicz et al., 1985; Lindstrom et al., 1990; Luetje and Patrick, 1991; McGehee and Role, 1995; Papke and Heinemann, 1991; Ramirez-Latorre et al., submitted; Role, 1992). Neuronal nAChRs were the first of the ligand-gated ion channels studied to display this degree of structural and functional complexity. Although nAChRs comprise only two distinct subunit types, there are multiple homologous forms of each subunit encoding gene. There are 8 neuronal "α" subunit genes (α1–α8) and 3 neuronal "β" subunit genes (β2–β4) cloned to date (Boulter et al., 1986; Heinemann et al., 1990; Nef et al., 1988; Seguela et al., 1993; Wada et al., 1989). With this array as a starting point, there could be more than $10^5$ varieties of pentameric nAChR complexes (McGehee et al., 1995 and Role, 1992). Study of native nAChRs indicates that the actual number of subunit combinations is less than theory would predict. Biochemical, immunochemical, and antisense deletion experiments to identify native compositions of nAChRs demonstrate that relatively few subunit combinations are likely to be found in native nAChRs. For example, the nAChRs expressed by autonomic and habenula neurons have been studied in detail (Brussard et al., 1994; Devay et al., 1994; Listerud et al., 1991; Clarke et al., 1986) and provide specific examples of the subunit composition of each nAChR channel subtype expressed. In view of the documented evolution of these neuronal nAChR channels during embryonic development, and the array of molecular and biophysical tools available to study these channels in detail, an understanding of the developmental regulation of nAChR subunit and channel subtype diversity may be close at hand. Numerous studies implicate the interaction during the formation of synaptic connections between the presynaptic and postsynaptic cells in the development of mature neuronal receptors (Arenella et al., 1993; Boyd et al., 1988; Brussaard et al., 1994b; Brussard et al., 1994; Devay (in preparation; Devay et al., 1994; Gardette, et al., 1991; Jacob 1991; Levey et al., 1994; Mandelzys et al., 1994; Moss et al., 1989).

Regulation of Neuronal Phenotype During Development: Contribution of Target Interactions Neuronal differentiation is induced by the interaction of developing neurons with target cells. One example is that of the evolution of transmitter phenotype in a special class of sympathetic neurons that evolve from an adrenergic to a cholinergic phenotype in the course of normal development. Although early on, these neurons synthesize, package and release catecholamines, the formation of synapses with the target sweat glands is accompanied by a change in transmitter expression that ultimately produces a mature cholinergic phenotype. This change in transmitter expression requires both pre- and postsynaptic signals. Thus, catecholamine release from the embryonic neuron is required to induce the release of a cell differentiation factor\leukemia inhibitory factor (CDF/LIF)-like factor called sweat gland factor (SGF) from the presumptive sweat glands. SGF, released via activation of target adrenergic receptors, interacts, with specific receptors on the innervating neuron. SGF induces the cellular machinery required for ACh synthesis and release in the presynaptic neuron. Thus, the attainment of a mature transmitter phenotype is regulated by both synaptic activity and target derived signals, offering an explanation for how the expression of the muscle-nAChR is eventually downregulated to a diffuse distribution. Elimination of muscle-nAChRs by innervation is accompanied by an increase in local synthesis, insertion and formation of high-density clusters of muscle-nAChR at the synaptic site. At later stages of synaptic development, there are marked changes in the biological properties of muscle-nAChR channels due to alterations in subunit gene expression. This produces "adult" type muscle-nAChR complexes of distinct subunit composition. Molecular signals that are believed to mediate these changes in muscle-nAChR distribution and synthesis have been identified and cloned, namely, agrin and AChR Inducing Activity (ARIA). Recombinant agrin alters the distribution of pre-existent muscle-nAChRs with no effect on synthesis or insertion of new receptors. In contrast, recombinant ARIA induces muscle-nAChR subunit gene expression, increasing the rate of appearance of new surface receptors from 3–5%/hr to 10–20%/hr.

It is possible that there are common regulatory mechanisms between nAChR and muscle-nAChR. It is believed that nAChRs on both CNS and PNS neurons evolve from low density and diffuse distribution to clustered and highly dense synaptic patches following innervation. Finally, like muscle-nAChRs, there are marked changes in the biophysical properties of nAChRs during development and presynaptic input may induce some of these changes, e.g., channel conductance and opening frequency.

Despite the essential role of ligand-gated ion channels in synaptic transmission between neurons, little is known about changes in their expression, function, distribution and subunit composition during neural development. Nicotine-induced enhancement of acquisition and consolidation of short term memories is believed to be mediated by innervation of target tissues regulates nAChR expression in CNS and PNS neurons.

This example is one of many implicating target-derived factors in the control of neuronal survival, proliferation, differentiation, migration, and neurite outgrowth. Although there are many factors that could mediate target effects on neuronal differentiation, the expression patterns and biological activities of factors identified to date identify a few candidates for proposed studies of nAChR regulation. (1) Ciliatory neurotropic factor (CNTF) mimics the effect of SGF in inducing a cholinergic phenotype. It has also been shown to promote differentiation of sympathetic precursor cells and likely participates in target-induced changes in nAChR expression. CNTF is expressed in numerous sympathetic targets including smooth muscle and kidney. (2) Activin and related members of the Transforming Growth Factor β (TGFβ) family, can also regulate the differentiation of the transmitter phenotype in autonomic neurons. These factors are expressed in sympathetic targets such as smooth muscle, sweat glands etc. (3) CDF/LIF mimics SGF by inducing a cholinergic phenotype. This factor is secreted by smooth muscle and heart muscle. Although less is known about either the activity or the distribution of these factors in the central nervous system (CNS), it is likely that CNS and peripheral nervous system (PNS) neurons may be regulated by similar signaling molecules.

Regulation of Receptor Synthesis and Distribution in Muscle: Contribution of Presynaptic Signals Classical studies of Fischbach, Cohen, and McMahan of the nerve-muscle junction demonstrate that the incoming motor nerve is a potent regulator of muscle-nAChRs. Prior to innervation, muscle expresses an embryonic form of nAChR which is diffusely distributed over the cell surface. The presynaptic nAChR activation since this activation facilitates a broad array of CNS synapses. In view of the impact that developmental changes in nAChRs have on neuronal excitability, synaptic efficacy and synaptic plasticity, studies of the regulatory controls of nAChR expression are essential. One avenue of study focuses upon the proteinaceous factors that appear to modulate receptor gene expression. One factor previously identified and cloned is heregulin (See Vandlen and Holmes, U.S. Pat. No. 5,367,060).

To date, 10 different proteins that result from alternative splicing of the heregulin gene have been described. Among these are the growth factors neu differentiation factor (NDF) (Wen et al., 1992), glial growth factor (GGF) (Marchionni et al., 1993), ARIA (Falls et al, 1993; Fischbach et al., 1994), and the heregulin isoforms (Holmes, 1992; Wen et al., 1994). The reported isoforms are principally membrane bound proteins which can be solubilized by proteolysis. The extracellular domains of these proteins consist of an N-terminal domain followed by an immunoglobulin-like (Ig-like) domain, a linker region, an EGF-like domain, and a second linker region (FIG. 5). These proteins are ligands for the epidermal growth factor (EGF) family of receptor tyrosine kinases. Binding of the ligand to the EGF receptor family members erbB3/HER3 or HER4 results in activation of the tyrosine kinase activity of the receptor. Other family members can be activated by trans-phosphorylation via the activated members.

Other members of the heregulin/NDF/ARIA family have been described in previous patent publications. PCT International Publication No. WO 94/08007, published Apr. 14, 1994, entitled "Trophic factor having ion channel-inducing activity in neuronal cells" describes neurotrophic factors designated as ARIA, which are able to induce the formation of ion channels. This publication also shows how ARIA is associated with both nervous tissue and skeletal muscle. ARIA has an Ig-like domain and an EGF-like domain in the extracellular region. U. S. Pat. No. 5,367,060, issued Nov. 22, 1994, entitled "Structure, production and use of heregulin", from U.S. Ser. No. 847,743, filed Mar. 6, 1992 by Richard L. Vandlen and William E. Holmes, discloses a polypeptide with a binding affinity for the $p185^{HER2}$ receptor. Vandlen and Holmes also disclose purification methods required to isolate heregulin and uses of the heregulins and antibodies specific to the heregulins as therapeutic agents. This polypeptide is related to but distinct from the ARIA protein.

SUMMARY OF THE INVENTION

This invention provides an isolated nucleic acid molecule encoding an nARIA polypeptide, including human nARIA (hnARIA) and chicken nARIA (cnARIA). These nucleic acid molecules may be DNA, cDNA, or RNA. This invention also provides for a purified nARIA polypeptide. This invention provides for a replicable vector comprising an nARIA sequence and host cells comprising this vector. This invention provides for a composition comprising the nARIA polypeptide and a pharmaceutically acceptable carrier. One embodiment of this invention is a method for inducing the formation of a synaptic junction between a neuron and a target cell comprising contacting the target cell with an nARIA polypeptide or a nucleic acid molecule encoding nARIA in an amount sufficient to induce the formation of a synaptic junction.

BRIEF DESCRIPTION OF THE FIGURES

FIGS. 1A–1C: Nucleotide sequence of chicken nARIA (SEQ ID NO:1).

A nucleic acid sequence encoding a splice variant from the heregulin gene is shown. This sequence is a compilation of the sequences derived from the ExoIII deletion series on the pBluescript II KS (+) subclone of phage #3 from a chick E13 total brain cDNA library screened with a rat pro-heregulin beta 1 probe generated by PCR amplification. The sequence was determined using the M13 reverse primer. The length is 3212 bases. The break in homology to the ARIA sequence occurs at a known splice site. The nucleotide sequences from base pair number 1293 downstream to the poly-A tail of the nARIA clone are identical to ARIA. The sequences upstream from base pair number 1293 encode a unique splice variant (i.e. bp 1293-bp 3212), nARIA.

FIG. 2: Amino acid sequence of chicken nARIA (SEQ ID NO: 2).

An amino acid sequence encoding a splice variant from the heregulin gene is shown. This sequence is a compilation of the sequences derived from the ExoIII deletion series on the pBluescript II KS (+) subclone of phage #3 from a chick E13 total brain cDNA library screened with a rat pro-heregulin beta 1 probe generated by PCR amplification. The sequence was arrived at using the M13 reverse primer. The length is 1070 amino acids. The asteriks denote unclear results at these stop codons.

FIG. 3: Nucleotide sequence of the unique portion of the human nARIA gene (SEQ ID NO: 3).

A nucleic acid sequence encoding the human nARIA (hnARIA) a splice variant from the heregulin gene, nARIA is shown. The product was subcloned into pBluescript II KS (+) the 5' end of the transcript is at the M13 end of the multiple cloning site (MCS). The length is 1351 bases. The unique portion of nARIA spans from base 93 to base 758.

FIG. 4: Amino Acid sequence of the unique portion of the human nARIA protein (SEQ ID NO: 4).

An amino acid sequence encoding the unique portion of the human nARIA is shown. The product was subcloned into pBluescript II KS (+) the 5' end of the transcript is at the M13 end of the MCS. The length is 449 amino acids.

Figure 5A:
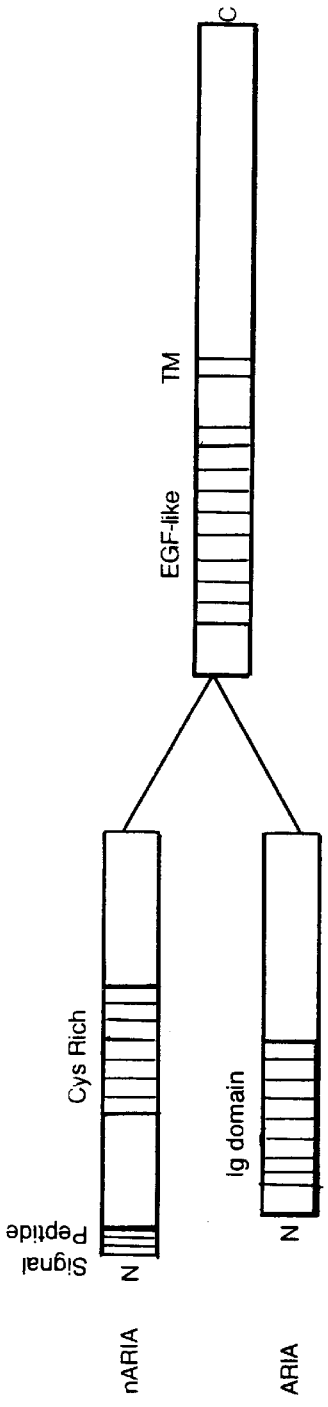
Figure 5B:
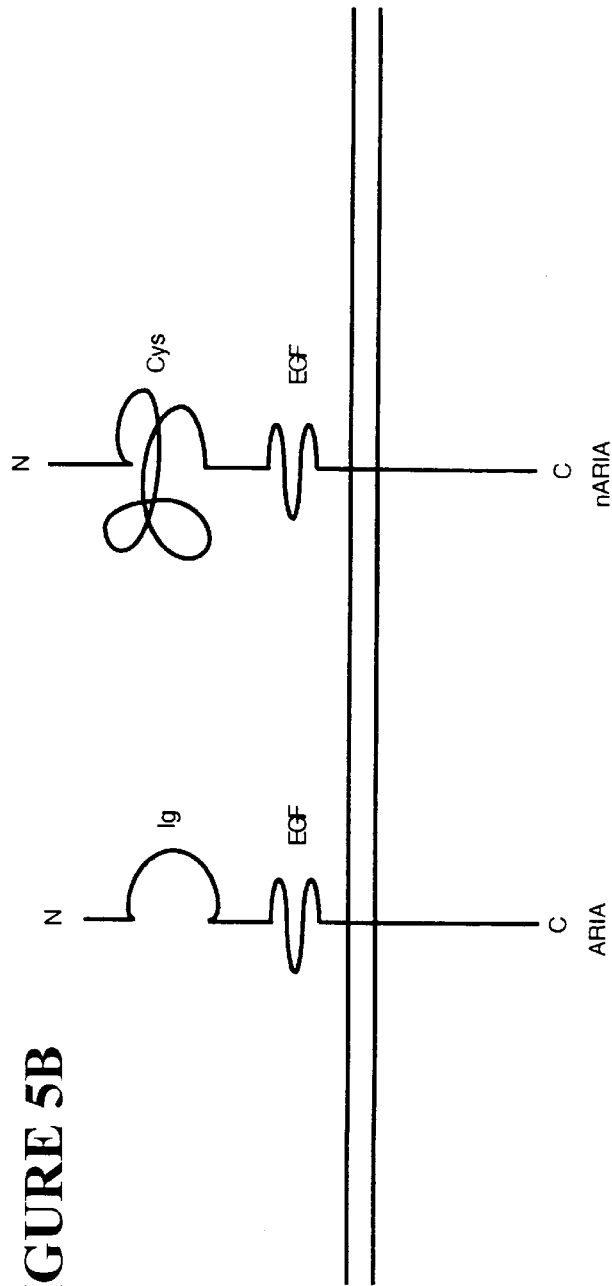

FIGS. 5A–5B: Comparison of gene structure of nARIA with ARIA (A) Comparison of the gene structure of the chicken nARIA cDNA with ARIA human nARIA, heregulin, and NDF. (B) Comparison of the exon structure of splice variants of the ARIA/NDF/Heregulin gene. The sequence we cloned (nARIA) has a unique N terminal domain devoid of Ig-like repeats common to other ARIA variants.

Figure 6:
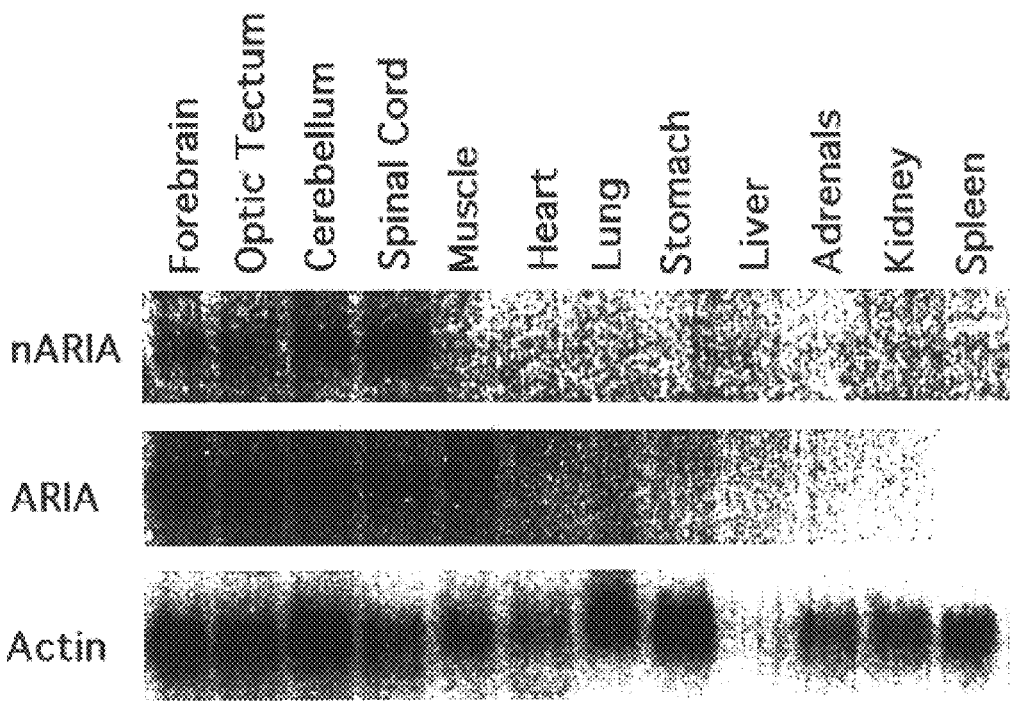

FIG. 6: Stage E13 multiple tissue Northern blot.

Multiple tissue Northern blots were screened with probes specific for unique domains of nARIA and were compared with those probed with an ARIA specific probe. The ARIA probe indicates that this form is present in skeletal muscle (pectoral muscle) whereas expression of nARIA is restricted to nervous tissue.

Figure 7:
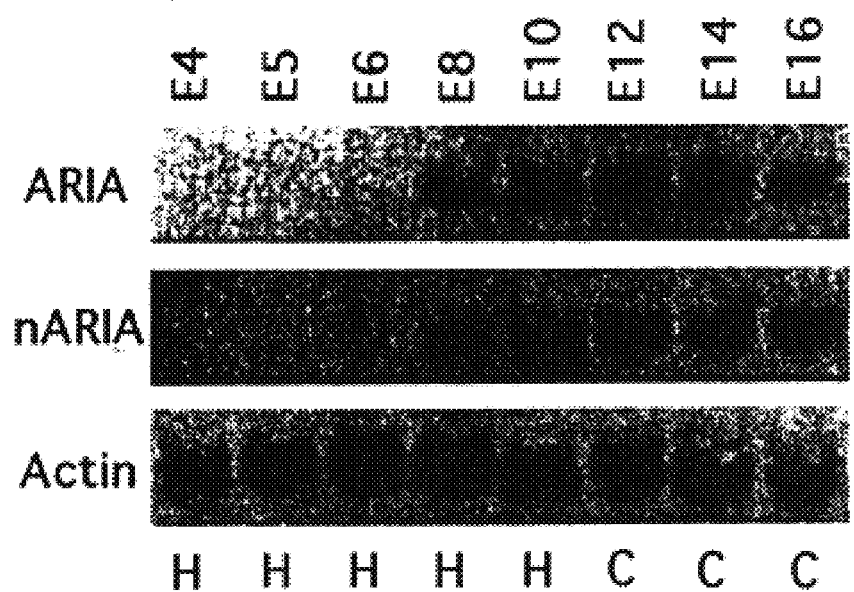

FIG. 7: Developmental Northern analysis of ARIA and nARIA in the chick hindbrain and cerebellum Northern blot analysis was performed on RNA samples from chick embryonic stages E4 through E16. Oligonucleotide probe specific for either nARIA or ARIA were used as probes. (H-hindbrain; C-cerebellum.)

Figure 8A:
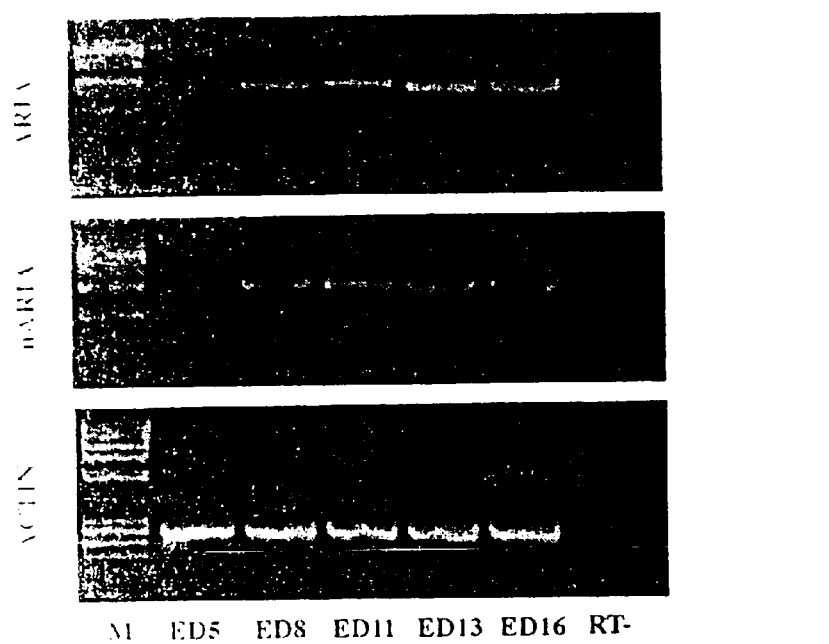
Figure 8B:
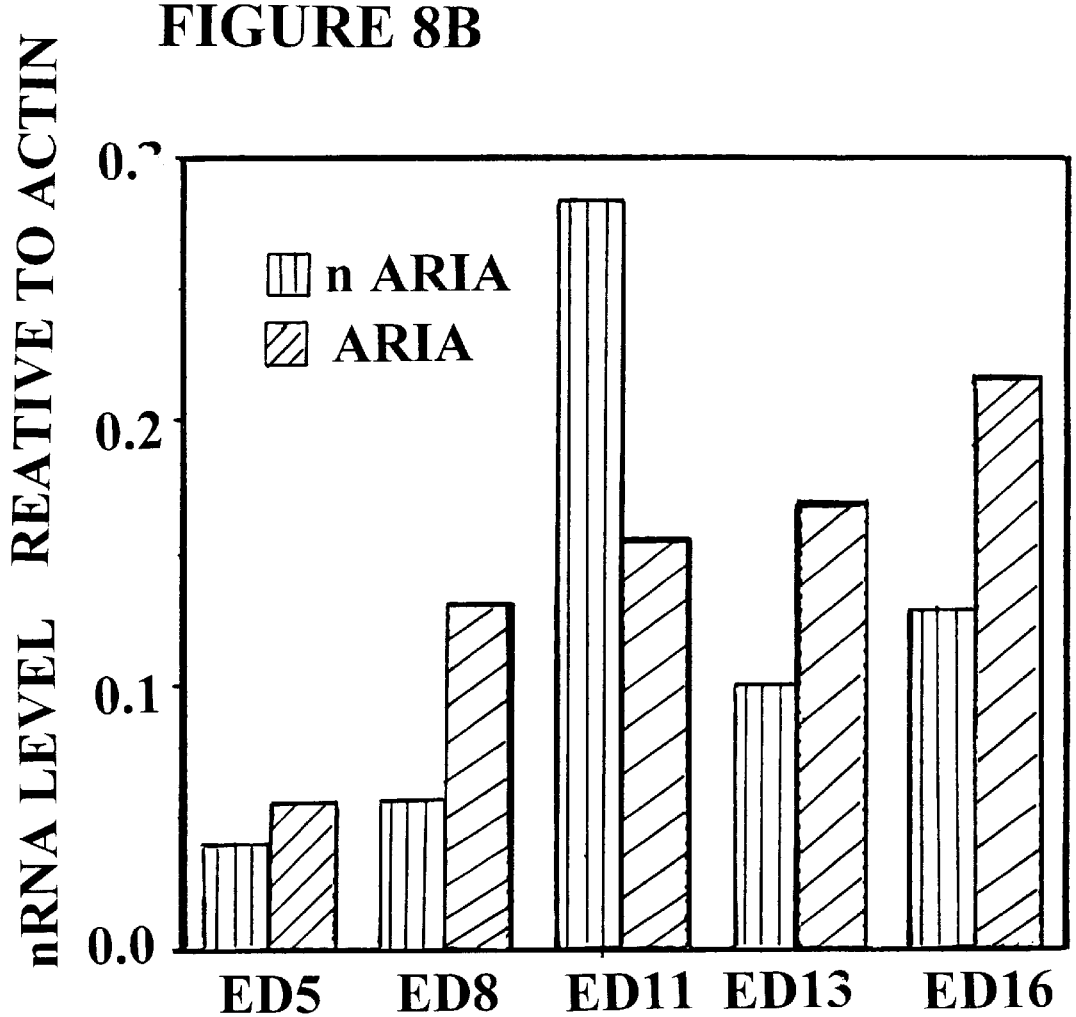

FIGS. 8A–8B: RT-PCR analysis of the developmental expression pattern of nARIA in the chick brain compared with ARIA.

(A) The developmental expression pattern of nARIA and ARIA in chick brain as detected by RT-PCR is shown. (B) Relative quantification of ARIA and nARIA mRNA levels normalized with actin mRNA levels is shown.

Figure 9A:
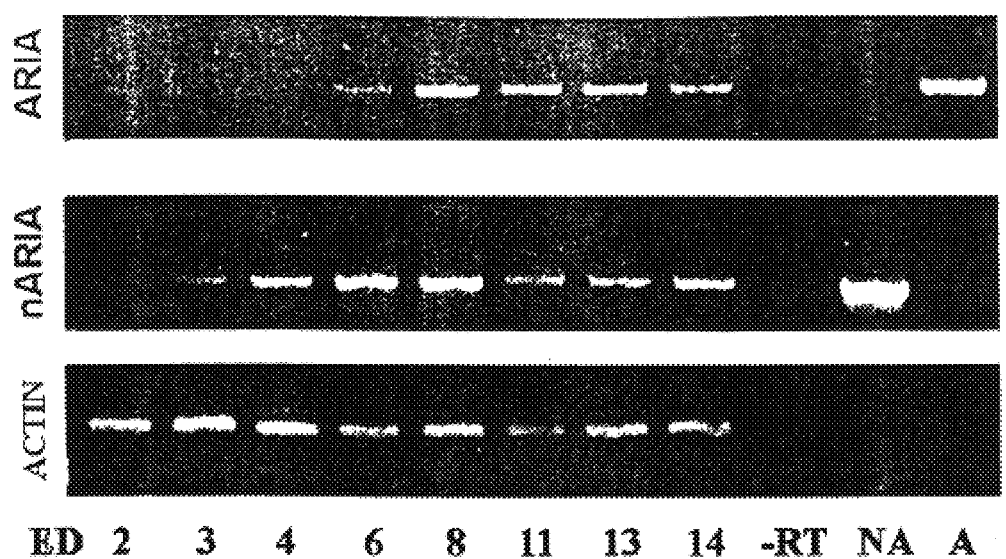
Figure 9B:
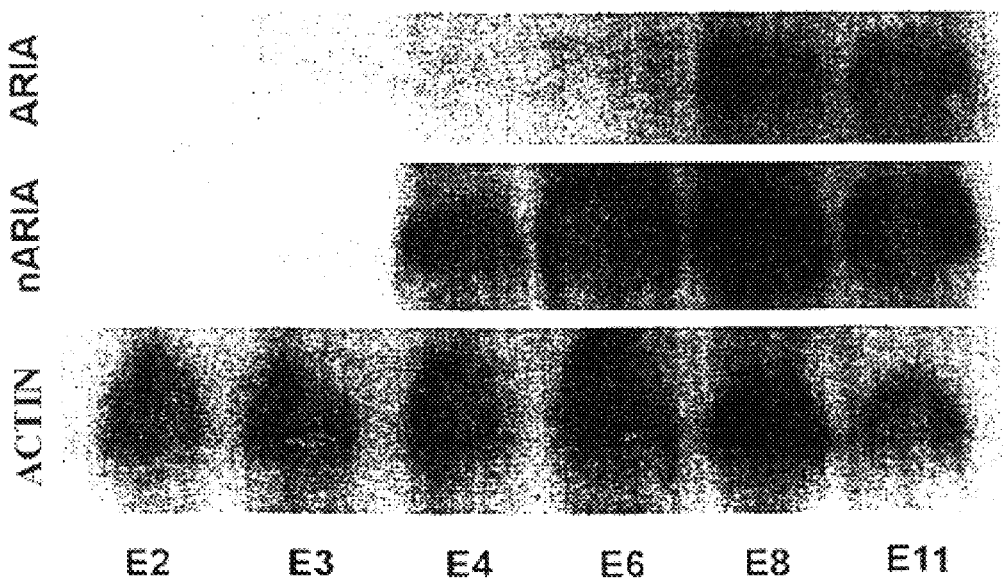
Figure 9C:
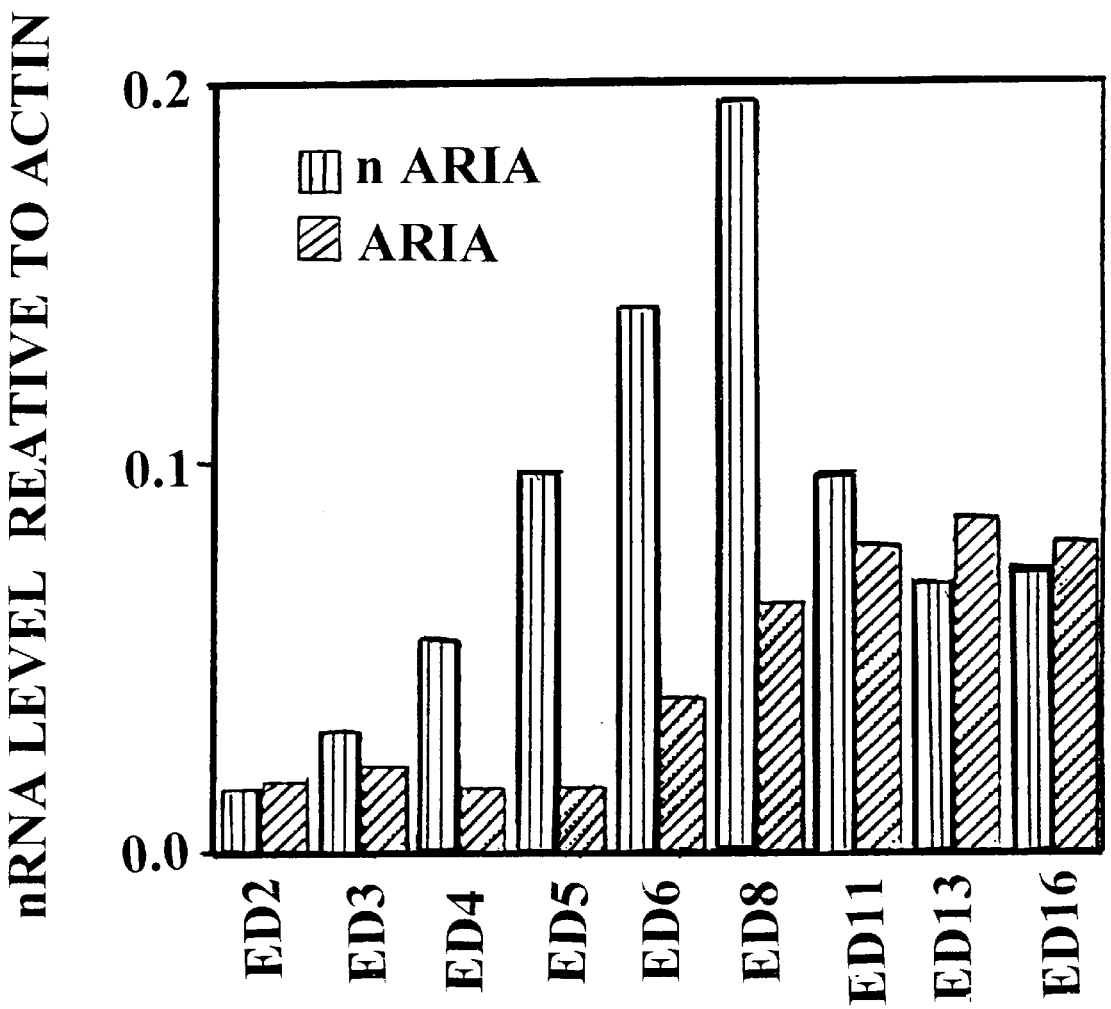
Figure 10A:
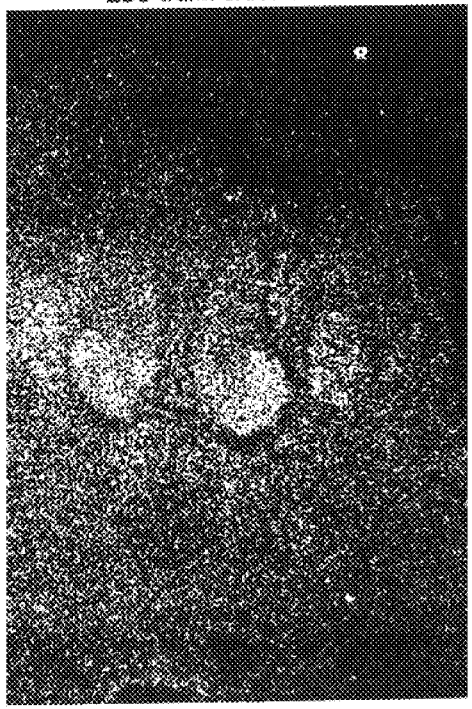
Figure 10B:
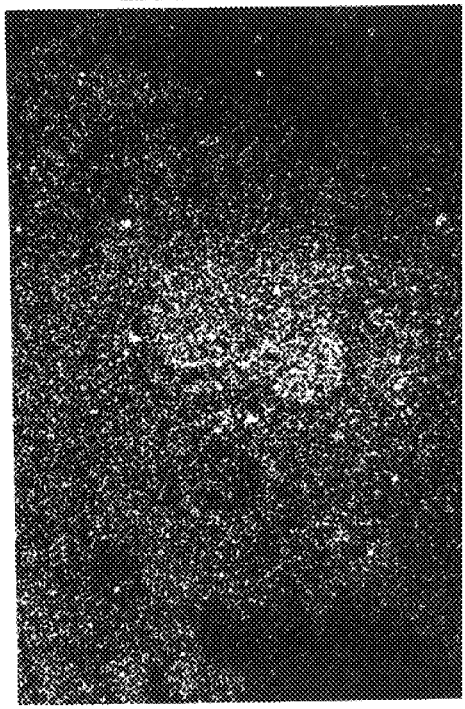
Figure 10C:
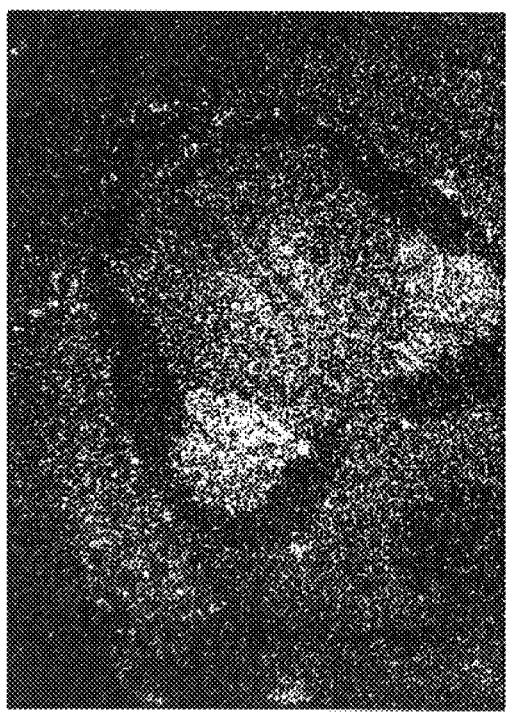
Figure 10D:
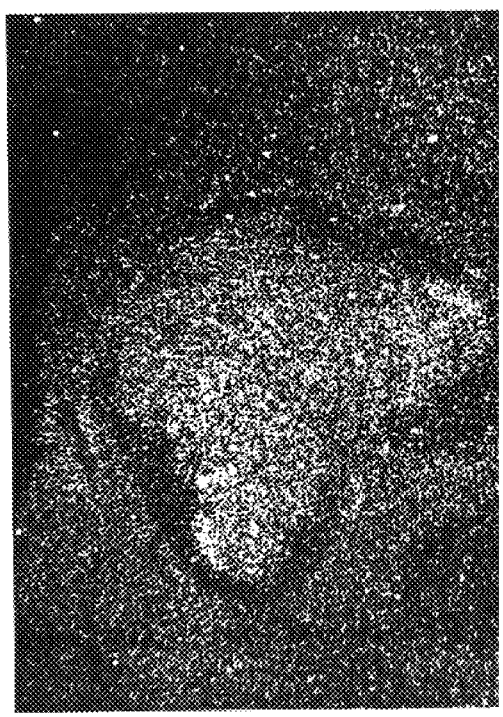

FIGS. 9A, 9B and 9C: nARIA and ARIA expression in the developing chick spinal cord as detected by PCR and Northern hybridization analysis.

(A) Northern blot of ARIA (top) and nARIA (bottom). All probes and primers are directed against sequences specific to nARIA and/or ARIA. Northern analysis indicates the mRNA of nARIA is detectable by E3 and robust by E4 whereas initiation of ARIA expression occurs later (E6–8) and is detectable at E6, but not robust until E8. (B) PCR detection of nRNA expression of ARIA and nARIA in developing chick spinal cord. Note specificity of primers tested on full length cDNAs (NA, A) (-RT: no reverse transcriptase reaction; NA—nARIA positive control; A—ARIA positive control). (C) Comparison of nARIA and ARIA mRNA levels relative to actin.

FIGS. 10A–10D: In situ hybridization of chick ED5 trunk cross-section of neural tissue with probes specific for nARIA and ARIA.

The probe specific for nARIA contains the Cys-rich domain and the probe specific for ARIA contains the Ig domain. Different patterns of expression are observed. A positive signal is observed in the presumptive preganglionic neurons with the nARIA probe but not with the ARIA probe. (A–D) ED5 trunk cross section. (A,C) nARIA specific probe. (B,D) ARIA specific probe.

FIGS. 11A, 11B and 11C: nARIA induces tyrosine phosphorylation.

(A) Phosphorylation of MCF7 cell line demonstrating activity of both recombinant ARIA and nARIA as ligands for tyrosine kinase-linked receptors. Dose (A) and time (C) dependence of ARIA (A) and nARIA (A,C) phosphorylations in MCF-7 cells. (B) Comparison of recombinant nARIA and ARIA tyrosine phosphorylation of E9 lumbar sympathetic ganglia (LSG).

Figure 12:
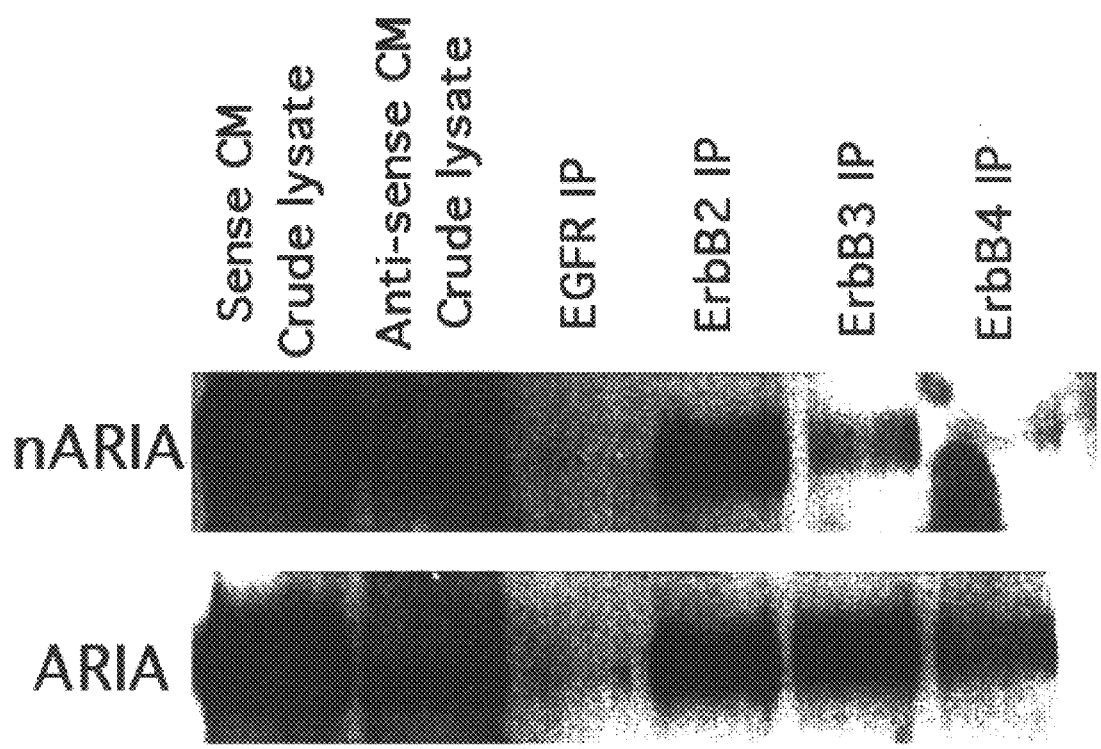
Figure 13A:
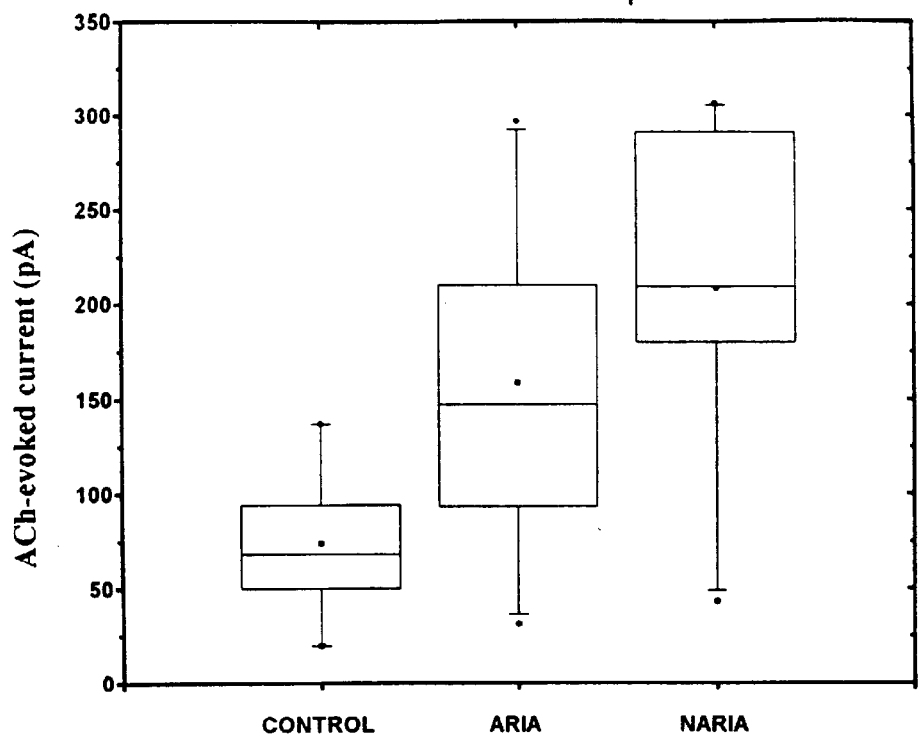
Figure 13B:
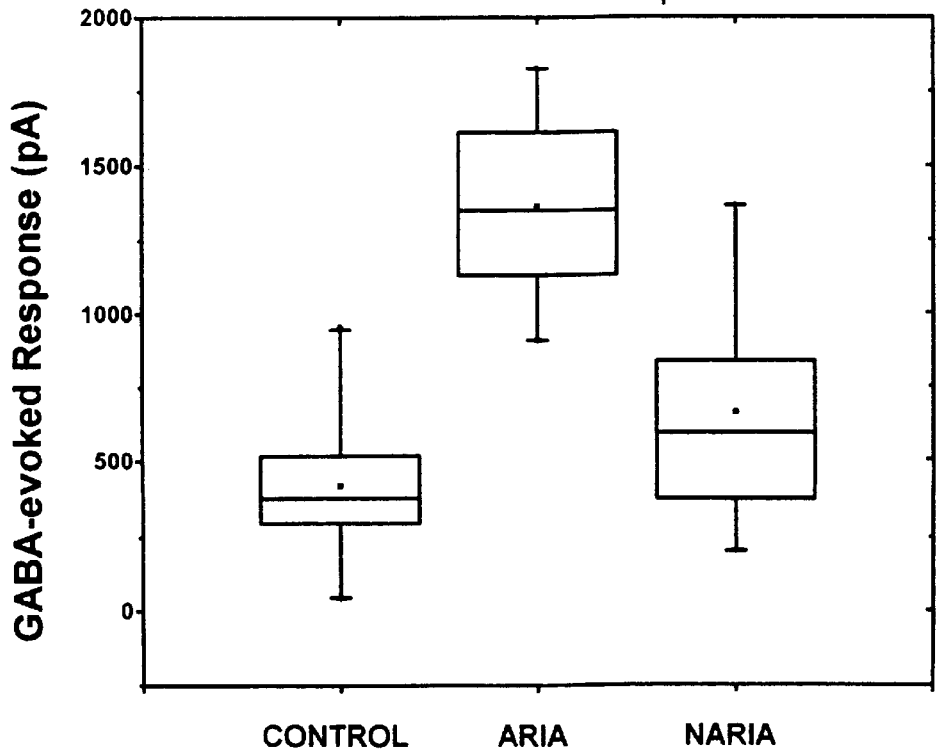

FIG. 12: Anti Phosphotyrosine Western Blot of MDA-MB-453 cells treated with conditioned media.

Media conditioned by COS1 or HEK293 cells transiently transfected with the nARIA clone (sense configuration) activates tyrosine kinase activity in the breast tumor cell lines MCF7 or MDA-MB-453 above the basal levels of tyrosine kinase activity (antisense configuration). The levels of phosphorylation of EGFR family members relative to one another was different between ARIA and nARIA.

FIGS. 13A–13D: Electrophysiological assay of transmitter gated macroscopic currents.

(A,C) ACh-evoked current. (B,D) GABA-evoked response. Treatment of primary cultures of sympathetic neurons from E11 chicks with recombinant nARIA for two days increases the magnitude of macroscopic currents activated by acetylcholine and appears to decrease the currents gated by GABA.

FIGS. 14A–14B: nARIA enhances expression of the nAChR subunit genes α3, α5, α7 and β4 and increases the magnitude of $I_{P(ACh)}$.

(A) Assay of nAChR subunit gene expression in E9 neurons maintained in vitro for 3 days and then treated for 24 hrs with 10 μl of recombinant nARIA (left) of ARIA (right) by quantitative RT-PCR. (B) Assay of $I_{P(ACh)}$ in E9 neurons maintained in vitro for 3 days and then treated for 48 hrs with 10 μl of recombinant nARIA or ARIA or antisense construct of each (control). Macroscopic currents evoked by 500 μM ACh. Peak current ($I_{P(ACh)}$) analyzed with non parametric tests appropriate for non-normally distributed values. Box-plots reveal the mid 50% of the data, whiskers delineate the 90% distribution. * indicates outliers.

Figure 15:
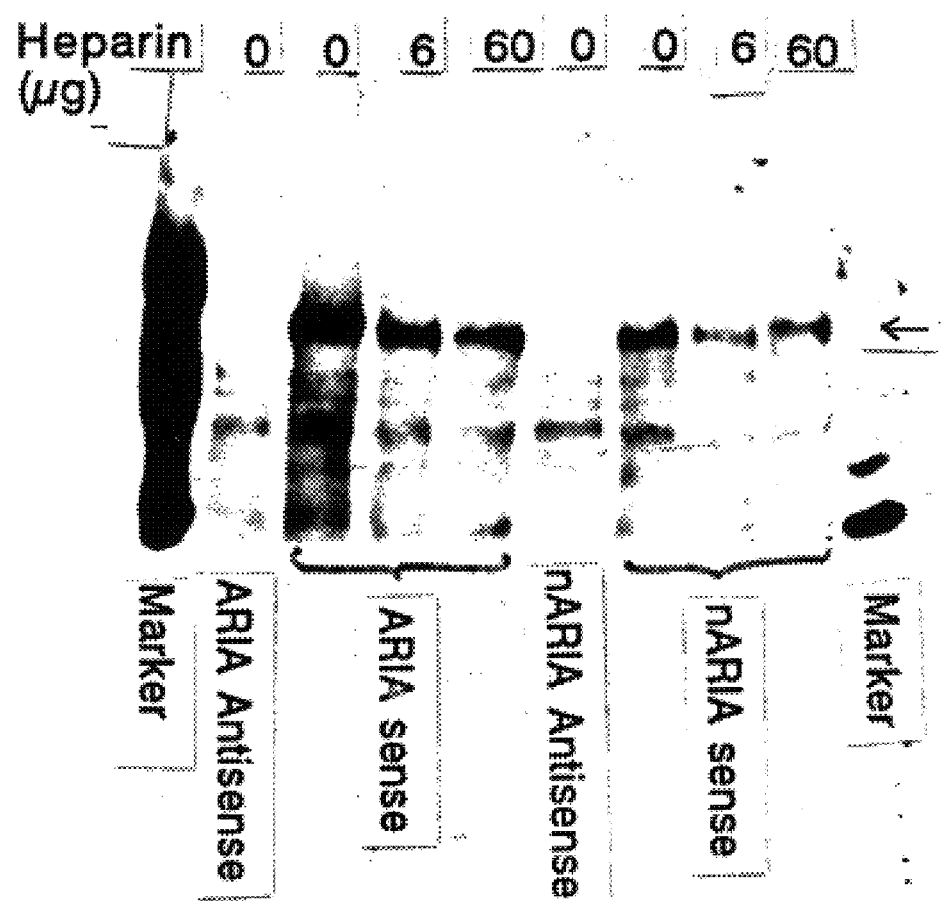

FIG. 15: Comparison of the affinity of nARIA vs ARIA for heparin sulfate proteoglycan.

MCF7 breast tumor cells were treated with conditioned media from either ARIA or nARIA transiently transfected COS1 cells. Some of the media was prebound with heparin attached to glass beads. Prior to treatment, the beads were pelleted by centrifugation to remove any heparin associated proteins. The supernatant was used to treat the MCF7 cells and tyrosine phosphorylation of the ARIA/nARIA receptor was analyzed.

Figure 16:
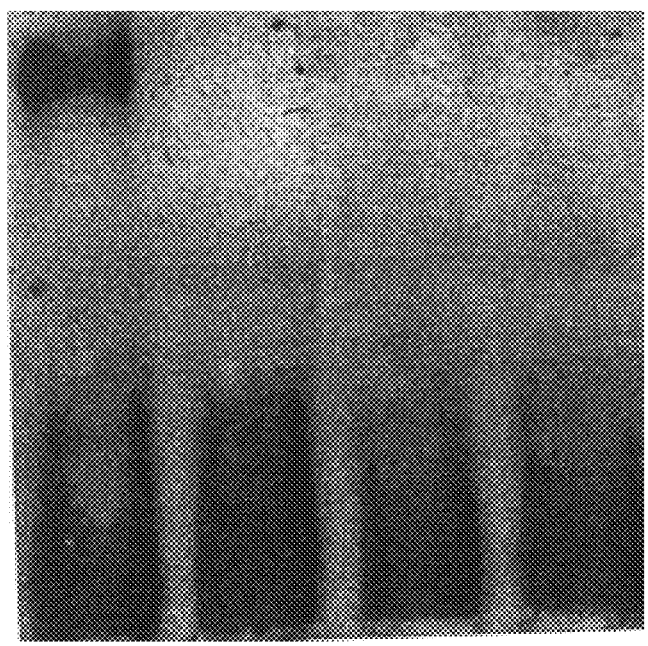

FIG. 16: The anti-nARIA antibody is specific for recombinant nARIA

Figure 17:
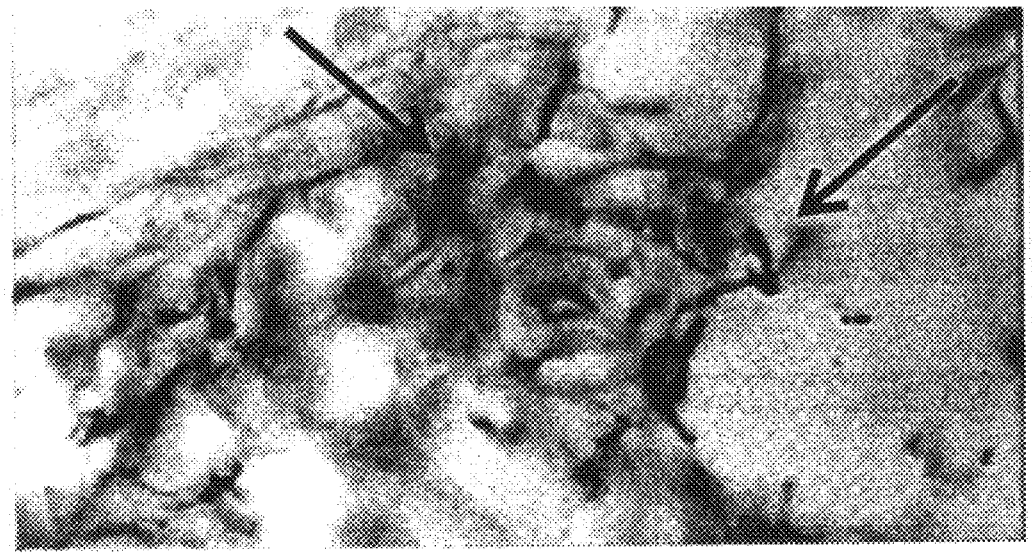

FIG. 17: Anti-nARIA antibodies reveal targeting of nARIA to axon terminals at CNS and PNS synapses FIG. 18: nARIA induction of nAChR expression is more potent than the Ig-containing isoforms.

Figure 19:
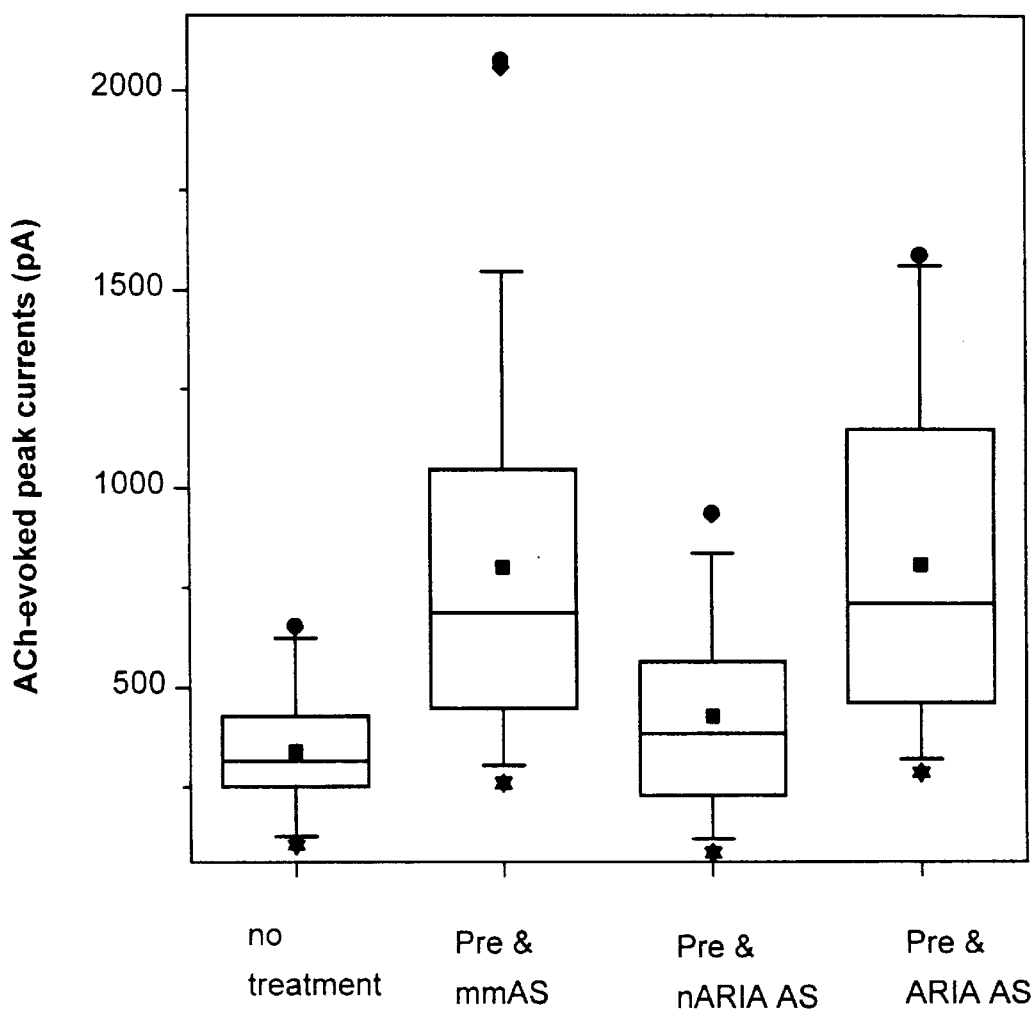

FIG. 19: Deletion of nARIA with isoform-specific antisense oligonucleotides reveals that nARIA is both necessary and sufficient for the regulation of nAChR expression by presynaptic input.

DETAILED DESCRIPTION OF THE INVENTION

This invention provides an isolated nucleic acid molecule encoding nARIA. This nucleic acid molecule may encode human nARIA (hnARIA), wherein the nucleic acid comprises the sequence shown from base 93 to base 758 of FIG. 3 (SEQ ID NO: 3). This invention also provides for an isolated nucleic acid molecule encoding nARIA, wherein the nucleic acid molecule encodes chicken nARIA (cnARIA) which comprises the sequence shown from base 608 to base 1234 of FIG. 1 (SEQ ID NO: 1). The nucleic acid molecule may be DNA, cDNA or RNA. The isolated nucleic acid molecule encoding nARIA includes nucleic acids encoding functionally equivalent variants or mutants of nARIA including nucleic acid molecules which, due to the degeneracy of the genetic code, code for nARIA polypeptide, such as the polypeptides shown in FIGS. 2 (SEQ ID NO: 2) and 4 (SEQ ID NO: 4).

The isolated nucleic acid molecule encoding nARIA includes nucleic acids encoding biologically active variants of nARIA. This includes nucleic acid molecules which are capable of specifically hybridizing with an nARIA sequence. Biologically active variants may include nucleic acid variants which have at least 75% amino acid sequence identity with an nARIA sequence, more preferably at least 80%, even more preferably at least 90% and most preferably at least 95w. Identity or homology with respect to an nARIA sequence is defined herein as the percentage of amino acid residues in the candidate sequence that are identical with nARIA residues in FIGS. 2 (SEQ ID NO: 2) and 4 (SEQ ID NO: 4) after aligning the sequences and introducing gaps, if necessary, to achieve the maximum percent homology, and not considering any conservative substitutions to be identical residues. None of N-terminal, C-terminal or internal extensions, deletions, or insertions into nARIA sequence shall be construed as affecting homology. The isolated nucleic acid molecule encoding nARIA also includes any splice variants having nARIA biological activity as defined hereinafter.

As used herein, the purified nARIA polypeptide includes biologically active nARIA polypeptides which include each expressed or processed nARIA sequence, fragments thereof having a unique consecutive sequence of at least 5, 10, 15, 20, 25, 30 or 40 amino acid residues as shown in the underlined regions in FIGS. 2 (SEQ ID NO: 2) and 4 (SEQ ID NO: 4). Biologically active amino acid variants of nARIA include a polypeptide wherein an amino acid residue has been inserted N- or C- terminal to, or within the nARIA sequence. Amino acid sequence variants include nARIA wherein an amino acid residue has been replaced by another residue, nARIA polypeptides including those containing predetermined mutations by, e.g. site-directed or PCR mutagenesis. nARIA includes nARIA from such species as rabbit, rat, porcine, non-human primate, Drosophila, equine, murine, opine, human and chicken and alleles or other naturally occurring variants of the foregoing; derivatives of nARIA wherein it has been covalently modified by substitution, chemical, enzymatic or other appropriate means with a moiety such as an enzyme or radioisotope. nARIA may be labeled with a detectable moiety including a fluorescent label, a biotin, a digoxigenin, a radioactive atom, a paramagnetic ion, and a chemiluminescent label. This invention also provides for glycosylation variants of nARIA (as in the insertion of a glycosylation site or deletion of any glycosylation site by deletion, insertion or substitution of an appropriate residue); and soluble forms of nARIA, such as nARIA which lacks a functional transmembrane domain.

As used herein, the purified nARIA polypeptide includes amino acid variants of nARIA which are prepared by introducing appropriate nucleotide changes into nARIA nucleic acid or by in vitro synthesis of the desired nARIA polypeptide. Such variants include, for example, deletions from, or insertions or substitutions of, residues within the amino acid sequence shown for human nARIA sequence. Any combination of deletions, insertion, and substitution can be made to arrive at the final construct, provided that the final construct possesses the desired characteristics. The amino acid changes also may alter post-translational modifications of nARIA, such as changes in the glycosylation sites, altering the membrane anchoring characteristics, altering the location of nARIA by inserting, deleting or otherwise affecting the transmembrane sequence of native nARIA or modifying its susceptibility to proteolytic cleavage.

This invention also provides for fusion proteins which contain nARIA polypeptide linked to an unrelated protein domain(s). The fusion proteins may be created by the insertion of amino- and/or carboxyl-terminal fusions ranging in length from one residue to polypeptides containing a hundred or more residues, as well as intrasequence insertions of single or multiple amino acid residues. Intrasequence insertions (i.e. insertions within the nARIA sequence) may range generally from about 1 to 10 residues, or preferably 1 to 5, and most preferably 1 to 3. Examples of terminal insertions include nARIA with an N-terminal methionyl residue (an artifact of the direct expression of nARIA in bacterial recombinant cell culture), and fusion of a heterologous N-terminal signal sequence to the N-terminus of nARIA to facilitate the secretion of mature nARIA from recombinant host cells. Such signal sequences generally will be obtained from, and thus be homologous to, the intended host cell species. Suitable sequences include STII or 1 pp for E. coli, alpha factor for yeast, and viral signals such as herpes gD for mammalian cells.

Other insertional variants of nARIA may include the fusion of the N- or C-terminus to an immunogenic polypeptide, e.g., bacterial polypeptides such as beta-lactamase or an enzyme encoded by the E. coli trp locus, or yeast protein, bovine serum albumin, or chemotactic polypeptides.

As used herein, the purified nARIA polypeptide includes amino acid substitution variants. These variants have at least one amino acid residue in the nARIA molecule removed and a different residue inserted in its place. The sites of greatest interest for substitutional mutagenesis include a site(s) identified as an active site(s) of nARIA, and sites where the amino acids found in nARIA ligands from various species are substantially different in terms of side-chain bulk, charge, and/or hydrophobicity.

The amino terminus region of the cytoplasmic region of the nARIA may be fused to the carboxy terminus of heterologous transmembrane domains and receptors, to form a fusion polypeptide useful for intracellular signalling of a ligand binding to the heterologous receptor.

Other sites of interest are those in which particular residues of the purified nARIA polypeptide obtained from various species are identical. These positions may be important for the biological activity of nARIA. These sites, especially those falling within a sequence of at least three other identically conserved sites, are substituted in a relatively conservative manner. Such conservative substitutions may be known as "preferred substitutions" and may include: valine substituted for alanine; lysine for arginine; glutamine for asparagine; glutamate for aspartate; serine for cysteine; asparagine for glutamine, aspartate for glutamate; proline for glycine; arginine for histidine; leucine for isoleucine; arginine for lysine, leucine for methionine, leucine for phenylalanine; glycine for proline, threonine for serine; serine for threonine; tyrosine for tryptophan; phenylalanine for tyrosine and leucine for valine.

Substantial modifications in function or immunological identity of the purified nARIA polypeptide are accomplished by selecting substitutions that differ significantly in their effect on maintaining (a) the structure of the polypeptide backbone in the area of the substitution, for example as a sheet or helical conformation, (b) the charge or hydrophobicity of the molecule at the target site, or (c) the bulk of the side-chain. Naturally occurring residues are divided into groups based on common side chain properties: hydrophobic; neutral hydrophilic; acidic; basic; residues that influence chain orientation and aromatic. Non-conservative substitutions will entail exchanging a member of one of these classes for another. Such substituted residues may be introduced into regions of nARIA that are homologous with other receptor ligands, or, more preferably, into the non-homologous regions of the molecule.

This invention provides for the creation of a combinatorial library of potential nARIA homologs which can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art (see Sambrook, et al., 1989; U.S. Pat. Nos. 5,223,409; 5,198,346 and 5,096,815. The purpose of making such a library is to provide in one mixture, all of the sequences encoding the desired set of potential nARIA sequences. This mixture could then be used for seletion of particular affinities, binding properties and separate functionalities.

This invention also provides for a replicable vector which contains nARIA sequence and a host cell containing this vector. This expression vector may be a prokaryotic expression vector, a eukaryotic expression vector, a mammalian expression vector, a yeast expression vector, a baculovirus expression vector or an insect expression vector. Examples of these vectors include PKK233-2, PEUK-C1, pREP4, pBlueBacHisA, pYES2, PSE280 or pEBVHis. Methods for the utilization of these replicable vectors may be found in Sambrook, et al., 1989 or in Kriegler 1990. The host cell may be a eukaryotic cell, a somatic cell, a germ cell, a neuronal cell, a myocyte, a mammary carcinoma cell, a lung cell, a prokaryotic cell, a virus packaging cell, or a stem cell.

This invention also provides for a purified polypeptide or an isolated polypeptide encoding nARIA. This polypeptide may encode human nARIA protein which includes the sequence shown from amino acid 31 to amino acid 252 of FIG. 4 (SEQ ID NO: 4). This polypeptide may also encode chicken nARIA protein which includes the sequence shown from amino acid 203 to amino acid 421 of FIG. 2 (SEQ ID NO: 2). This invention provides for the genomic sequence of human nARIA and chicken nARIA. This invention provides for functionally equivalent variants or mutants of nARIA including polypeptides which contain replacement amino acids which do not affect the functionality of the polypeptide. These variants may be prepared using in vitro mutagenesis techniques, polymerase chain reaction mutagenesis, or site-directed mutagenesis. The invention also provides for nARIA derivatives in vitro which are immobilized on a support for purposes of diagnoses, purification of nARIA binding factors or affinity purification of nARIA antibodies.

According to the present invention, nARIA or neuronal Acetylcholine Receptor Inducing Activity possesses certain biological activities. As used herein, nARIA has the ability to increase both nAChR currents and nAChR subunit gene expression in LSG neurons. The sequence of nARIA is unique throughout the N-terminal portion of the sequence, lacking the Ig-like domain typically upstream of the EGF-like domain in ARIA. nARIA retains the juxtamembrane EGF-like domain, shown to be sufficient for receptor binding and activation of receptor tyrosine kinase activity. Expression of nARIA by Northern blot analysis begins at E4 and is maximal at E8, while expression of ARIA begins at E6 and peaks at E8 in the chick embryo. In cultured E11 chick sympathetic neurons treated with cultured media from COS cells transiently transfected with either ARIA or nARIA, an assay of both acetylcholine (ACh) gated currents and subunit mRNA levels was performed. These assays demonstrated differential regulation of nAChRs by nARIA vs ARIA. Specifically, nARIA significantly increased the maximal responses to 500 mM ACh whereas ARIA significantly decreased the maximal responses compared to cultures treated with recombinant protein from the antisense construct. Measurement of nAChR subunit mRNA levels in E9 sympathetic neurons treated with nARIA or ARIA with quantitative RT-PCR revealed different profiles of subunit gene regulation. A 24 hour treatment with nARIA mimicked the effects of innervation, up-regulating $\alpha 3$, $\alpha 5$, $\alpha 7$ and $\beta 4$ levels, whereas ARIA downregulated $\beta 4$ and $\alpha 3$. nARIA, therefore, may participate in the increase in nAChR subunit transcription induced by innervation of embryonic sympathetic neurons in vivo during sympathetic neuronal development.

nARIA, as discussed herein, not only has a unique N-terminal region but also displays biological activity distinct from ARIA. Tables I, II and III in the Experimental Details section herein describe these distinctions. nARIA, unlike ARIA, is specifically expressed only in nervous tissue, whereas ARIA can be expressed in other tissues. nARIA expression is higher in the spinal cord and cerebellum than in the forebrain and optic tectum. nARIA expression is first detected at stage E4 in the spinal cord, and expression is first detected in the cerebellum at stage E8. In E11 sympathetic neurons, nARIA specifically has an effect on ligand gated channels: in response to acetylcholine, nARIA specifically increases the number of functional acetylcholine receptors as indicated by an increase in response to maximal concentrations of acetylcholine. nARIA has little effect on the number of GABA activated channels as indicated by the response to maximal concentrations of GABA. In contrast, at E11, ARIA has little effect on acetylcholine evoked resonses and may upregulate GABA evoked responses. The effects of nARIA and ARIA on the acetylcholine evoked responses indicates that nARIA has been quantitated at E9 and is about 15 times more potent than ARIA.

nARIA increases the transcription of the $\alpha 3$ subunit of nAChR in sympathetic neurons. nARIA also increases $\alpha 5$, $\alpha 3$, $\alpha 7$ and $\beta 4$ subunit gene expression of nAChR.

This invention provides for a method of inducing the expression of a specific nicotinic acetylcholine receptor subunit isoform. AChRs at mature mammalian neuromuscular junctions are pentameric protein complexes composed of four subunits in the ratio of $\alpha_2\beta\epsilon\delta$ (Mishina et al 1986). Most, if not all, of embryonic AChRs contain a different subunit, termed "$\tau$" in place of the $\epsilon$ subunit. When mixtures of $\alpha$, $\beta$, $\delta$ and $\tau$ subunit mRNAs are injected into *Xenopus oocytes,* the expressed channels have the properties of embryonic receptors. It is likely that this change in subunit composition is due to a change in gene expression and accounts for the switch in properties of ACh-activated channels from slow channels to fast channels. This invention provides for the application of nARIA alone or in combination with another agent to neural cells to induce the expression of subunit isoforms.

This invention further provides for nARIA antagonists which are capable of reducing the biological activity of nARIA. This antagonist may be proteinaceous such as an antibody specific for nARIA as described herein, a nucleic acid such as an antisense molecule to the nARIA mRNA as described herein, an enzymatic activity such as a ribozyme directed to nARIA mRNA as described herein or a protease specific for the nARIA polypeptide. The antagonist may also be an agent which is capable of binding the nARIA receptor with higher affinity than nARIA, thus competing away the effects of nARIA binding.

The subject invention also provides for nARIA agonist(s) which would be capable of enhancing the biological activity of nARIA. Such agonists may include other neurotrophic factors such as ciliary neurotrophic factor (see U.S. Pat. No. 4,997,929); nerve growth factor (see U.S. Pat. No. 5,169,762); neurotrophic factor 4/5 (see PCT International Publication No. WO 92/05254); brain-derived neurotrophic factor (see U.S. Pat. No. 5,180,820); glial-derived neurotrophic factor (see PCT International Publication No. WO 93/06116) or any other neurotrophic factor (see European application EP 0 386 752 A1). The disclosures of these publications in their entireties are hereby incorporated by reference into this application in order to more fully describe the state of the art as known to those skilled therein as of the date of the invention described and claimed herein.

This invention also provides for an antibody immunoreactive with an epitope comprising a unique sequence shown in either FIG. 2 from amino acid 203 to amino acid 421 or in FIG. 4 from amino acid 31 to amino acid 252.

A further embodiment of the invention is a monoclonal antibody which is specific for nARIA. In contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. Also, they may be used to remove nARIA from the serum. A second advantage of monoclonal antibodies is that they can be synthesized by hybridoma cells in culture, uncontaminated by other immunoglobins. Monoclonal antibodies may be prepared from supernatants of cultured hybridoma cells or from ascites induced by intraperitoneal inoculation of hybridoma cells into mice. The hybridoma technique described originally by Kohler and Milstein, 1976, has been widely applied to produce hybrid cell lines that secrete high levels of monoclonal antibodies against many specific antigens.

Another embodiment of this invention is a ribozyme which is capable of cleaving nARIA mRNA. See Cech, et al., U.S. Pat. No. 4,987,071; Altman et al., U.S. Pat. No. 5, 168,053; Haseloff et al, U.S. Pat. No. 5,254,678 published European application No. Hampel et al., EP 360,257.

This invention provides for a nucleic acid comprising a unique nARIA sequence in a 3' to 5' orientation, antisense to at least a portion of a gene encoding naturally occurring nARIA. This antisense nucleic acid molecule may be labeled with a detectable moiety selected from the group consisting of a fluorescent label, a biotin, a digoxigenin, a radioactive atom, a paramagnetic ion, and a chemiluminescent label. See Inoue et al. U.S. Pat. Nos. 5,208,149 and 5,190,931 and Schewmaker, U.S. Pat. No. 5,107,065.

Labeling of a circular oligonucleotide (such as a replicable vector as described herein) can be done by incorporating nucleotides linked to a "reporter molecule" into the subject circular oligonucleotides. A "reporter molecule", as defined herein, is a molecule or atom which, by its chemical nature, provides an identifiable signal allowing detection of the circular oligonucleotide. Detection can be either qualitative or quantitative. The present invention contemplates using any commonly used reporter molecule including radionucleotides, enzymes, biotins, psoralens, fluorophores, chelated heavy metals, and luciferin. The most commonly used reporter molecules are either enzymes, fluorophores, or radionucleotides linked to the nucleotides which are used in circular oligonucleotide synthesis. Commonly used enzymes include horseradish peroxidase, alkaline phosphatase, glucose oxidase and $\alpha$-galactosidase, among others. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1.2-phenylenediamine, 5-aminosalicylic acid or toluidine are commonly used. The probes so generated have utility in the detection of a specific nARIA DNA or RNA target in, for example, Southern analysis, Northern analysis, in situ hybridization to tissue sections or chromosomal squashes and other analytical and diagnostic procedures. The methods of using such hybridization probes are well known and some examples of such methodology are provided by Sambrook et al, 1989. This invention also provides a method of amplifying a nucleic acid sample comprising priming a nucleic acid polymerase chain reaction with nucleic acid (DNA or RNA) encoding (or complementary to) an nARIA.

Another embodiment of this invention is the normal expression or overexpression of nARIA ex vivo in human neuronal cells, stem cells or undifferentiated nerve cells and muscle cells. These cells may be utilized for gene therapy in patients (See Anderson et al U.S. Pat. No. 5,399,346).

This invention further provides for a transgenic nonhuman mammal whose germ or somatic cells contain a nucleic acid molecule which encodes nARIA polypeptide or biologically active variants thereof, introduced into the mammal, or an ancestor thereof, at an embryonic stage. This invention provides for a transgenic nonhuman mammal whose cells may be transfected with a suitable vector with an appropriate sequence designed to reduce expression levels of nARIA polypeptide below the expression levels of that of a native mammal. The transgenic nonhuman mammal may be transfected with a suitable vector which contains an appropriate piece of genomic clone designed for homologous recombination. Alternatively, the transgenic nonhuman mammal may be transfected with a suitable vector which encodes an appropriate ribozyme or antisense molecule. See for example, Leder and Stewart, U.S. Pat. No. 4,736,866 for methods for the production of a transgenic mouse.

Biologically functional variants of nARIA are nucleic acid molecules that, due to the degeneracy of the genetic code, code on expression for nARIA polypeptide. The foregoing variant DNA sequences may be translated into variant nARIA polypeptides which display the biological activity of an nARIA polypeptide. These variant nucleic acid molecules may also be expressed in this transgenic mammal. Active variants should hybridize to the wild-type nARIA nucleic acid sequence under highly stringent or moderately stringent conditions (Sambrook et al, 1989).

One embodiment of this invention is a method for inducing the formation of a synaptic junction between a neuron and a target cell, which includes treating the target cell with nARIA polypeptide or nARIA nucleic acid molecule encoding nARIA or a biologically active variant thereof, in an amount sufficient to induce the formation of a synaptic junction. A "sufficient amount" as used herein refers to that amount which provides a therapeutic effect for a given condition and administration regimen. The target cell may be a somatic cell such as a myocyte, a neuronal cell, a glandular cell or any postsynaptic cell. This method provides for the induction of the formation of a synaptic junction in an individual having a neurological disorder involving abnormal synaptic connections. Isolated nARIA may be used as a growth factor for in vitro cell culture or in vivo to promote the growth of cells.

nARIA, nARIA agonists or nARIA antagonists may be used to treat any disease where levels of nARIA metabolism are changed and therefore ion channel levels or activities are not normal as in some neurological disorders. Such disorders would include any disease with an abnormal production of nARIA. Neurological disorders that affect the central nervous system, memory or cognitive functions may also be treated with nARIA. Such disorders may be the result of the normal aging process or the result of damage to the nervous system by trauma, surgery, ischemia, infection or metabolic disease. Such disorders may also include Alzheimer's Disease, Turret's Syndrome, and Parkinson's Disease. These diseases have been shown to respond to nicotine treatment.

The neurological disorder may be a neuromuscular disorder. Examples of neuromuscular disorders which may be treatable with nARIA include Alzheimer's disease, myasthenia gravis, Huntington's disease, Pick's disease, Parkinson's disease, and Turret's Syndrome. Also included are neurogenic and myopathic diseases including chronic atrophies such as amyotrophic lateral sclerosis, Guillain-Barre syndrome, progressive bulbar palsies, spinal muscular atrophies and chronic peripheral neuropathy. Autonomic disorders of the peripheral nervous system may also be included in this treatment which include disorders that affect the innervation of muscle or endocrine tissue such as tachycardia, atrial cardiac arrhythmias and hypertension. These disorders are thought to be associated with an abnormally low level of muscarinic AChRs in the striated muscle.

This invention provides for a method of altering neuro-receptor expression. In this method, nARIA is administered to a subject which may result in a change in the expression of neuro-receptors. The method of administration of nARIA is described more fully hereinafter.

This invention provides for the production of functional mammalian NARIA protein in a prokaryotic expression system, a mammalian expression system, a baculovirus expression system, an insect expression system or a yeast expression system. This production may provide for the post-translational modifications which exist in the naturally occurring nARIA protein. For protocols describing bacterial expression of mammalian proteins, see Sambrook et al, 1989.

Another embodiment of this invention is a method for inducing neuronal regeneration which comprises contacting a target cell with a composition of nARIA and a pharmaceutically acceptable carrier to induce the formation of a synaptic junction between a neuron and a target cell. The target cell may be a neuronal cell, an endocrine cell, a muscle cell or any cell capable of forming a neuro-muscular junction. nARIA may be used to facilitate incorporation of implants into nervous tissue or to promote nerve regeneration following damage by trauma, infarction, infection or postoperatively.

This invention provides for a combination therapy of nARIA with another neurotropic factor or cytokine or growth factor or with other agents known for use in the treatment of malignancies. Such factors may include transforming growth factor beta (TGF-β), ciliary neurotropic factor (CNTF), brain derived neurotropic factor (BDNF), NT-4, NT-5, NT-4/5, nerve growth factor (NGF), activins, agrin, cell differentiation factor (CDF), glial growth factor (GGF), and neu differentiation factor (NDF), ARIA, and heregulins. nARIA may be administered in combination with agrin for effects on the neuromuscular junction. For therapy directed toward the autonomic/enteric nervous system, TGF-β and nARIA is the preferred combination. For therapy directed to the central nervous system, nARIA and CDF is the preferred combination.

When administered parenterally, proteins are often cleared rapidly from the circulation and may therefore elicit relatively short-lived pharmacological activity. Consequently, frequent injections of relatively large doses of bioactive proteins may by required to sustain therapeutic efficacy. Proteins modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified proteins (Abuchowski et al., 1981; Newmark et al., 1982; and Katre et al., 1987). Such modifications may also increase the protein's solubility in aqueous solution, eliminate aggregation, enhance the physical and chemical stability of the protein, and greatly reduce the immunogenicity and antigenicity of the protein. As a result, the desired in vivo biological activity may be achieved by the administration of such polymer-protein adducts less frequently or in lower doses than with the unmodified protein. nARIA compositions may be administered parenterally by injection or directly into the cerebral spinal fluid by continuous infusion from an implanted pump. nARIA may also be administered with one or more agents capable of promoting penetration of nARIA across the blood-brain barrier.

Attachment of polyethylene glycol (PEG) to proteins is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous proteins. For example, a PEG adduct of a human protein might be useful for the treatment of disease in other mammalian species without the risk of triggering a severe immune response. nARIA or cells that produce nARIA may be delivered in a microencapsulation devise so as to reduce or prevent an host immune response against the nARIA producing cells. nARIA may also be delivered microencapsulated in a membrane, such as a liposome.

Polymers such as PEG may be conveniently attached to one or more reactive amino acid residues in a protein such as the alpha-amino group of the aminoterminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

Another embodiment of this invention is a method for determining a prognosis of or diagnosing a neoplastic condition in a subject. In this method, one may obtain a biological sample from the subject, and contact the sample with a reagent capable of binding to an element in the sample, the element being an nARIA nucleic acid molecule or polypeptide encoding nARIA, under conditions such that the reagent binds only if the element is present in the sample. One may then detect the presence of the reagent bound to the element and thereby determine the prognosis of the neoplastic condition of the subject. The reagent may be an oligonucleotide capable of hybridizing with a nucleic acid encoding nARIA polypeptide under standard stringency hybridization conditions. The reagent in this method may be an antibody specific for nARIA polypeptide. The element in the biological sample may be a nucleic acid molecule encoding nARIA or a polypeptide encoding nARIA protein. The biological sample may be cerebrospinal fluid, blood, plasma, ascites fluid, tissue, urine, sputum, amniotic fluid, saliva, lung lavage, or cell extracts. This method may be performed with the reagent is affixed to a solid support. The neoplastic condition may be a mammary neoplasm or a small cell carcinoma of the lung.

A further embodiment of this invention is a method for treatment of a neoplastic condition of a subject. In this method a pharmaceutically acceptable form of nARIA in a sufficient amount over a sufficient time period is administered to a subject to induce differentiation of neoplastic cells and thus treat the neoplastic condition. The composition may be a form of nARIA such as nARIA polypeptide or nARIA nucleic acid, combined with a pharmaceutically acceptable carrier. The carrier may be made up of suitable diluents, preservatives, solubilizers, emulsifiers, or adjuvants and may be in an aerosol, intravenous, oral or topical form.

Also provided by the invention are pharmaceutical compositions comprising therapeutically effective amounts of polypeptide products of the invention together with suitable diluents, preservatives, solubilizers, emulsifiers, adjuvants and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of nARIA. The choice of compositions will depend on the physical and chemical properties of the protein having nARIA activity. For example, a product derived from a membrane-bound form of nARIA may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and nARIA coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal, oral, injection or infusion by intravenous, intraperitoneal, intracerebral, intramuscular, intraocular, intraarterial or intralesional. nARIA may be part of a pharmaceutical composition with agrin and an acceptable carrier to recapitulate both the induction of expression of AChR and the clustering of the AChR's on the membrane surface.

Polypeptides of the invention may be "labeled" by association with a detectable marker substance (e.g., radiolabeled or biotinylated) to provide reagents useful in detection and quantification of nARIA or its receptor bearing cells in solid tissue and fluid samples such as blood or urine.

Another embodiment of this invention is a method for determining whether a compound is capable of modulating the binding of an nARIA polypeptide to its receptor. In this method, the compound may be incubated under suitable conditions with an appropriate nARIA polypeptide-affinity derivative or receptor-affinity derivative under appropriate conditions such that an affinity complex may form. Then, one may measure the amount of affinity complex formed so as to determine whether the compound is capable of modulating the binding of the nARIA polypeptide to its receptor. The affinity complex may be an nARIA receptor bound to an affinity derivative or an nARIA polypeptide bound to a derivative. The measurement in this method may comprise binding of an antibody specific for nARIA to the affinity complex to measure the amount of affinity complex formed. The affinity derivative may be sepharose, cellulose, plastic, glass, latex, glass beads, a nylon membrane, a cellulose acetate membrane, an epoxy-activated synthetic copolymer membrane, a nitrocellulose membrane or a streptavidin-coated plastic.

This invention is illustrated in the Experimental Detail section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Isolation and Sequence Analysis of nARIA

Novel members of the ARIA/NDF/heregulin family that would be expressed in neurons projecting to cholinoceptive neural targets were identified. Cloning efforts yielded 29 positives, including several which encoded variants with an entirely novel N-terminal sequence, distinguished by the absence of the usual Ig-like domains of the heregulin/NDF family. The predominance of the novel, Ig-less clones over the ARIA like clones was striking (11 vs 5 of 29 positives). We named the novel splice variant "nARIA" for neuronal nAChR Inducing Activity. All clones were isolated by two different and separate approaches as described below.

A different library was used in each screening protocol carried out to isolate and clone the nARIA gene. A chick E13 total brain cDNA library was screened with a rat DNA probe generated by PCR amplification. For the PCR amplification, degenerate primers corresponding to nucleotide sequences 523–542 (upper primer) and 1080–1100 (lower primer) of the published rat NDF sequence (Wen et al., 1992) were used to amplify a DNA fragment from a template of adult rat spinal cord cDNA. The upper and lower primers were within the immunoglobulin and transmembrane domains respectively. The amplified fragment was subcloned into the PCRII® vector (Invitrogen) and was sequenced, revealing an open reading frame. The predicted peptide encoded by this fragment contained the immunoglobulin to transmembrane domains of the heregulin β1 isoform and is distinct from the published NDF sequence, which is an α-isoform of heregulin. Screening of the cDNA library by random primed labeling of the amplified fragment resulted in three independent clones, of which only one contained a complete open reading frame. This open reading frame is 2055 nucleotides (FIG. 1, nucleotides 608–2662) and encodes the nARIA transcript. The nucleotide sequences from base pair 1293 downstream to the poly-A tail of the nARIA clone are identical to ARIA a related cloned chicken gene (Falls et al., 1993).

On the protein level, identical sequences encode the portion of the molecule spanning from the EGF-like domain to the C-terminus in ARIA and NARIA. The break in homology occurs at a known splice site and the sequences upstream to the splice junction are unique to nARIA. Analysis of the predicted protein sequence did not produce a motif corresponding to an immunoglobulin domain. Instead, there was a cysteine rich region identified (8 cysteines in 34 amino acids). See FIG. 2.

EXAMPLE 2

Spatial and Temporal Expression of nARIA in Chick Development

A chick E5-E11 spinal cord cDNA library which we prepared was also screened. The probe for screening was generated by RT-PCR amplification from E8 chick spinal cord total RNA using primers corresponding to nucleotide sequences 264–281 (upper primer) and 1294–1313 (lower primer) of the published ARIA sequence (Falls, et al., 1993). The amplified PCR fragment was subcloned into a PGEM3Z vector and sequenced to confirm its identity. Screening of the chick E5–11 spinal cord primary cDNA library by random primed labeling using the PCR fragment as the template resulted in 26 clones. Of these, 11 contained the novel cysteine rich domain (nARIA like clones), 6 clones contained the immunoglobulin-like domain (ARIA like splice forms), while the remaining clones had unidentifiable sequences. The nARIA clones included 8 that were identical to the form obtained by the earlier screening and 3 additional isoforms that differed in the N-terminus, the EGF-like domain, the juxtamembrane linker, and/or the C-terminal region. The extracellular domains of these clones were fully sequenced and the intracellular portions were partially sequenced. Restriction mapping and Southern blotting were also used to confirm the relatedness of these molecules. A human cerebellar cDNA library was screened in the manner described above. This procedure resulted in the isolation of human nARIA FIGS. 3 and 4 (SEQ ID NO: 3 and 4 respectively).

Multiple tissue Northern blots were screened with probes specific for unique domains of nARIA and were compared with those probed with an ARIA specific probe (FIG. 6). In particular, the ARIA probe detected ARIA in skeletal muscle (pectoral muscle) whereas expression of nARIA was found to be restricted to nervous tissue. The expression of nARIA represents a higher percentage of the total message in the cerebellum and spinal cord than in the forebrain or optic tectum. ARIA message is represented at a higher level in the forebrain and optic tectum than in the cerebellum and spinal cord (FIG. 7). The developmental expression patterns of nARIA and ARIA in spinal cord as detected by RT-PCR and Northern blot hybridization are different (FIGS. 8A–8B). The mRNA of nARIA is detectable by E3 and robust by E4 whereas initiation of ARIA and expression occurs later (E6–8) (FIGS. 9A–C).

In situ hybridization studies with probes specific for nARIA and ARIA (containing the cysteine rich domain or Ig-like domain respectively) also demonstrated different patterns of expression (FIGS. 10A–D). In particular, a positive signal is obtained in the presumptive preganglionic neurons with the nARIA probe but not with the ARIA probe. Therefore, the pattern of expression of ARIA and nARIA are different.

EXAMPLE 3

Functional Analysis of Biological Activity—nARIA Activates Tyrosine Kinase Linked Receptor(s)

Initial experiments to characterize the functional properties of the nARIA protein focused upon the ability to activate protein tyrosine kinases. ARIA has been proposed to act, as other members of the NDF/heregulin family, through an interaction with specific tyrosine kinase-linked receptors (Falls, et al., 1993). This first step in transduction is assayed as tyrosine phosphorylation of a high molecular weight band, thought to represent phosphorylation of the receptor subunit(s). We examined the pattern of tyrosine phosphorylated proteins in extracts of lumbar sympathetic ganglia (LSG) neurons as well as several other cell lines with an anti-TYR-P antibody (4G10; UBI) (Ausubel et al., 1994; Falls, et al., 1993). Both recombinant ARIA and nARIA (from transiently transfected COS cells) induced time and dose dependent phosphorylation of 170–185 kD bands in the MCF7 and MDA-MB-453 cell lines (human carcinomas that overexpress erb-B2 receptor). ARIA appeared more potent than nARIA and somewhat less robust in phosphorylation of a 185 kD band in LSG. Differential effects of nARIA on glial cells and neurons differ from all other heregulin isoforms including ARIA, examined to date. nARIA's unique N-terminal sequence influences the binding of the isoform to the protein tyrosine kinase receptors thereby conferring distinct specificities.

Media conditioned by COS1 or HEK293 cells transiently transfected with the nARIA clone (sense configuration) activated tyrosine kinase activity in the breast tumor cell lines MCF7 or MDA-MB-453 above the basal levels of tyrosine kinase activity as determined by using the antisense configuration of nARIA. See FIGS. 11A–C. Furthermore, the levels of phosphorylation of the EGFR family members relative to one another was different between ARIA and nARIA. ARIA treatment resulted in a higher level of erB3/HER3 phosphorylation than nARIA. Treatment of acutely dispersed sympathetic neurons from E9 chicks with nARIA conditioned media resulted in increased tyrosine phosphorylation of an approximately 180 kD protein (FIG. 12).

Another assay to more clearly delineate between the biological activities of nARIA and ARIA involved the comparison of their effects on the expression of ligand-gated channels in primary neurons. These studies assayed the number of functional surface receptors for two transmitters (ACh and GABA) using an electrophysiological assay of transmitter gated macroscopic currents. The rationale for these experiments is based upon the pattern of expression of nARIA and ARIA, and on our previous studies of receptor regulation by spinal cord neurons (Role, 1988; Gardette et al, 1991). Treatment of primary cultures of sympathetic neurons from E11 chicks with recombinant nARIA for two days increased the magnitude of macroscopic currents activated by acetylcholine and appeared to decrease the currents gated by GABA (FIGS. 13A–D). In contrast, treatment with recombinant ARIA under the same conditions decreased the currents gated by acetylcholine and appeared to enhance GABA-evoked currents. The differential effects of nARIA vs ARIA on ACh gated currents, an index of the number of functional channels on the cell surface, was also reflected in the assays of the levels of expression of ACh receptor subunit encoding mRNA's.

Notably, a 24 hour treatment with recombinant nARIA increased the level of α3 subunit mRNA; in contrast, the level of α3 subunit mRNA was either slightly decreased or not altered by ARIA. The differential effect of nARIA and ARIA on transcription was not limited to the acetylcholine receptor subunits. Application of the differential display technique to primary cultures of sympathetic neurons treated for 24 hours with nARIA or ARIA suggested that the two growth factors differentially activate or suppress transcription of several distinct cDNAs.

The data presented herein suggests that the novel splice variant of the heregulin gene, nARIA may play a role in synaptic development that is unique from that of ARIA or other immunoglobulin-domain-containing splice variants. nARIA may potentially be used therapeutically or diagnostically. Alterations in the level of the production of nARIA may be indicative of a traumatic insult to the nervous system. Since the receptor for this factor is a known oncogene, changes in growth factor levels may be prognostic to some neoplastic conditions. Recombinant nARIA may be useful in cancer treatment regimens or for use in neuronal regeneration as described more fully herein. Other isoforms have been demonstrated to induce differentiation of breast tumor cell lines, promote survival of glial cells and increase the mitogenesis of some cell lines.

It has been demonstrated that the biological activity of nARIA is different than that of ARIA and is summarized in Table I. (The bold serves to highlight the differences in biological activity between ARIA and nARIA.)

TABLE I

Biological Activity and Effects of ARIA vs nARIA

| Biological Activities | ARIA | nARIA |
|---|---|---|
| Expression | Seen in chick nervous tissues and skeletal muscle | Seen only in nervous tissue at E13 |
|  | Expression is higher in the forebrain and optic tectum than in the spinal cord and cerebellum | Expression is higher in the spinal cord and cerebellum than in the forebrain and optic tectum |
|  | Expression starts at E6 in the spinal cord | Expression starts at E4 in the spinal cord |
|  | Expression starts at E8 in the cerebellum | Expression starts at E8 in the cerebellum |
| Activation of p185 phosphorylation | Seen in L6 rat myocytes | Seen in L6 rat myocytes |
|  | Seen in PC12 cells (Fischbach, et al) | Not seen in PC12 cells |
|  | Seen in sympathetic neurons | Seen in sympathetic neurons |
|  | Seen in ciliary neurons (Fischbach, et al) | Not determined |
|  | Seen in breast tumor cell lines MCF7 and MDA-MB-453 | Seen in breast tumor cell lines MCF7 and MDA-MB-453 |
|  | Seen in rat O2A cells (Fischbach) | Not determined |
| Effects on ligand gated channels | Increases response to acetylcholine in E9 and decreases response in E11 sympathetic neurons | Increases response to acetylcholine in E9 and increases response in E11 sympathetic neurons |
|  | Increases response to GABA in E9 and increases response in E11 sympathetic neurons. | Increases GABA responses in E9 and decreases responses in E11 sympathetic neurons |
|  | Increases response to ACh in muscle cells (Fischbach et al.) | Not determined |
| Effects on transcription of nAChR subunits in rat medial habenula | No effect | Not determined |
| Effects on transcriptio | No effect on α3 Increases α5 and α7 | Increases α3 Increases α5 and α7 |

TABLE I-continued

Biological Activity and Effects of ARIA vs nARIA

| Biological Activities | ARIA | nARIA |
|---|---|---|
| n of nAChR subunits in sympathetics | | |
| Effects on sodium channel in muscle | Increases (Fischbach et al.) | Not determined |
| Effects on PC12 differentiation | Induces very short neurites in 10% of the cells (Fischbach et al.) | Not determined |
| | Reduces rate of replication by half (Fischbach et al.) | Not determined |
| Effects on glial cells | Increases the number of oligodendrocytes that develop from O2A precursors (Fischbach et al.) | Not determined |
| Effects on nAChR subunits in PC12 cells | "Like control" (Fischbach et al.) | Not determined |

Macroscopic, Single Channel and Synaptic Current Data Acquisition and Analysis Single channel data acquisition and analysis was performed with an Axon Instruments system using Axobasic and PCLAMP 6.0 software. Additional programs were specifically designed for resolution of multiple channel classes of similar size and kinetics. Conductance, kinetics, NPO and mean I analyses were performed as previously described (Listerud et al., 1991; Moss and Role, 1993; Moss et al., 1989; Simmons et al., 1988). Continuously recorded and evoked synaptic and macroscopic currents were stored on videotape and analyzed off line in software written in Axobasic.

An 80486 DX2–66 Mhz computer equipped with the Axobasic system was essential to all studies. The acquisition program sampled all events that conformed to the amplitude and rise-time criteria, both set up by the user. Each captured trace included 20 msec of pre-event baseline data. The system sampled events accurately up to 20 Hz—entirely adequate for capturing the relatively low frequency events in the experiments described herein. The analysis software provides amplitude, frequency, rise- and decay-time constant information for each current recorded.

Subsequent generation of histograms, cumulative plots fitting, and statistical analyses were performed with Microsoft Excel 3.0, Sigmaplot 4.1 (Jandel Scientific) and Systat. Synaptic current frequency information was divided into bins for plotting and statistical comparisons. Statistical analyses of differences between control and treatment groups were evaluated by a two-tailed test (Snedecor and Cochran, 1989). Synaptic current amplitude data were compared by plotting cumulative histograms. These plots were also utilized as estimated cumulative probability distributions for the determination of statistically significant differences between treatment groups using the Komolgorov-Simirnov test (Press et al., 1986).

Table II provides a comparison of synaptogenesis vs. recombinant nARIA or ARIA treatment in regulating nAChR gene expression. (Bold serves to highlight the differences.)

TABLE II

Comparison of Synaptogenesis vs. Recombinant nARIA or ARIA treatment in regulating nAChR gene expression.

| AChR subunit | α2 | α3 | α4 | α5 | α7 | β2 | β4 |
|---|---|---|---|---|---|---|---|
| Development in vivo | ND | 170% | ↓ to ND | 500% | 1000% | +/− | 600% |
| Presynaptic input in vitro | — | 240% | — | 315% | 150% | — | 195% |
| Target contact in vitro | — | ↓; 60% of control | | 189% | 261% | ? | no▲ |
| Heart | | | | | | | |
| Kidney | | 148% | | 160% | 150% | | 143% |
| recombinant N-ARIA | — | 224% | — | 248% | 372% | ? | [0–400%] |
| recombinant ARIA | — | ↓; 90% of control | — | 265% | 215% | ? | no▲ |

Table III provides a comparison of the regulation of ACh-gated currents induced by input and target vs nARIA and ARIA.

TABLE III

Comparison of the Regulation of ACh-Gated Currents Induced by Input & Target vs. nARIA and ARIA.

| Presynaptic input in vitro | | Target Contact in vitro: | |
|---|---|---|---|
| SMN | ↑1300% | Heart | ↓30% of control |
| VMN Input Cond. Media | ↑750% | Target Cond. Media | |
| SMN | ↑420% | Heart | ↓50% of control |
| VMN recombinant nARIA | ↑430% ↑200–400% | Kidney recombinant ARIA | ↑225% ↓60% of control |

Experimental Methods

Cell Culture

LSG Co-cultures With Presynaptic Input and Target.

Dissociated embryonic sympathetic neurons from ED10 and ED17 were prepared and maintained in vitro as described in Role 1988 with modifications as noted herein. Under these conditions the neurons were devoid of nonneuronal cells and were both adrenergic and cholinoceptive. Innervation of sympathetic neurons by preganglionic microexplants was done according to previously described techniques (Gardette et al. 1991; Hasselmo and Bower, 1993). Assay of target effects on nAChR expression required coculture of atrial micro-explants (ED12) with LSG neurons in vitro. Changes in expression of subunit mRNAs were assayed after 3–4 days of coculture by quantitative RT-PCR (see below and Habecker and Landis, 1994).

Patch Clamp Recording

Recording of macroscopic and synaptic currents employed the whole-cell tight seal recording configuration of the patch clamp technique (Hammil et al., 1981). This techniques provided low noise recordings that allowed for resolution of elemental synaptic currents. Fabrication of patch electrodes, pipette and bath solutions were all as previously described (Moss and Role, 1993; Moss et al., 1989). Currents were recorded with an AXOPATCH 200A patch clamp amplifier and stored on videotape with a PCM digitizer (Instrutech VR-10B) for subsequent analysis off line. $I_{P(AChR)}$ is peak current.

Drug Application

Drugs and agonists were applied by microperfusion to small groups of cells via a large barreled delivery tube with continuous macroperfusion at 1 ml/min. This approach optimized speed of application (<30 msec), speed of removal and the ease of changing test solutions applied by the same device. A stable perfusion set-up was an essential component of the each recording set up.

Molecular Techniques

Identification of Subunit Gene Expression by PCR

The profile of subunit gene expression was analyzed by PCR amplification of cDNA using nAChR subunit specific primers according to our previously published techniques (Listerud et al., 1991). Briefly, total RNA was extracted by homogenization of tissue in 4M guanidine thiocyanate buffer followed by centrifugation through a 5.7M CsCl cushion. The isolated RNA was DNAse treated and reverse transcribed using oligo-dT primers. AMV-RT(reverse transcriptase) was used to amplify a fragment encoding the most variable portion of the nAChR subunits, the intracellular loop. The identity of the amplified products was verified by restriction mapping and/or Southern blotting (Ausubel et al., 1994).

Quantitative RT-PCR

Cell contents were collected by aspiration into DEPC containing solution and cDNA was synthesized by addition of random hexamer primers and Superscript® reverse transcriptase enzyme (BRL). The cDNA served as template for amplification by primers specific for the various nAChR subunits. The internal standard construct included sequences complimentary to all upstream and downstream primers used with an interposed multicloning site (MCS) linker. Thus, the efficiency of primer annealing to standard and to the cDNA template was equivalent. In order to detect the product of the reaction, trace amounts of isotope labeled nucleotides were added to the reaction mixture. After 23 rounds of amplification, an aliquot of the reaction mixture was removed and further amplified with fresh Taq polymerase and reaction mix. This step was repeated after another 23 cycles. The amplified fragment was separated from the unincorporated nucleotides by electrophoresis and the product was quantitated. The assay provided subunit specific quantification of α2, α3, α4, α5, α7, α8, β2 and β4 in individual samples which detected as little as 2 fg of each subunit.

COS Cell Transfection

Cells were tansfected according to established techniques (Falls et al., 1993). Briefly, pcDNAl-amp containing the nARIA or ARIA cDNA in sense or antisense orientation was introduced into COS cells using lipofectamine® (Gibco-BRL) per manufacturer's instructions. Twenty-four (24) hrs after transfection, the cells were washed and incubated in serum-free OPTI-MEM® (Gibco-BRL). After 48 hrs, the media was collected, centrifuged to remove debris and then concentrated 22-x using a Centriprep® 10 concentrator (Amicon). Aliquots were stored at −20° C. until use.

Tyrosine-phosphorylation Assay

Cells were treated with L-15 media plus concentrated conditioned media from either sense, antisense, or non-transfected COS cells. After the desired incubation time, the cells were washed and lysed in 1% NP-40 buffer. The lysate was centrifuged and the protein in the supernatant was quantified with a Bradford analysis procedure (BioRad). Protein samples were electrophoresed on a 4% SDS-PAGE gel and electroblotted onto a PBDF membrane (S&S Inc). Then the membrane was probed for phosphotyrosine with a monoclonal antibody 4G10 (UBI), detected with a peroxidase-conjugated anti-mouse $IgG2_b$ antiserum (Boehringer-Mannheim) and visualized using the luminescent ECL® reagents (Amersham)

In situ Hybridization

Cell-specific expression of AChR subunit mRNAs were assayed using in situ hybridization in tissue sections of spinal preganglionic nuclei with $^{35}$S-labeled complementary RNA probes as described (Devay et al., 1994; Ausubel et al, 1994). cDNAs encoding the non-conserved regions between transmembrane-spanning regions, TM3 and TM4, for each subunit have been subcloned into pGEM-3Z plasmids. Antisense riboprobes were transcribed in the presence of $^{35}$S-UTP using the Promega transcription kit. Hybridization was assayed by autoradiography, and Nissl staining allowed visualization of the cell bodies. $^{35}$S-labeled RNA probes provided good signal resolution with low background due to the high specific activity (cpm/probe molecule) and also due to the relatively low energy of $^{35}$S emission. Determination of hybridization involved comparison between parallel assays with antisense cRNA, sense RNA and RNase pre-treatment of the tissue. Non-isotopic labeling protocol utilizing Digoxigenin-11-UTP in place of the $^{35}$S -UTP was also used. The protocols were very similar (Bertrand et al., 1991).

Antisense Oligonucleotide Design and Experimental Protocols

Antisense oligonucleotides for AChR subunits α2, α3, α4, α5 and α7 were targeted to a 15 base sequence spanning the initiation site of each subunit mRNA. The region upstream and including the ATG was divergent among the subunit sequences and in no case included <4 base mismatch with all chick cDNA sequences registered in GCG. Control oligos included missense sequences of identical composition of oligos mutated at 3 of the 15 bases (same GCG ratio). The uptake, metabolism, hybridization and block of subunit expression by oligonucleotides were studied in some detail to determine optimal conditions for specific block. Briefly, neurons were pretreated with an irreversible nAChR ligand (bromoacetylcholine bromide; BAC) and then incubated for 6–48 hrs with 10 μM oligo in heat inactivated medium) (Gardette et al., 1991; Listerud et al., 1991). The d-oligos were taken up and intact 15-mer within the cells was maximal within 6 hrs and still detected up to 48 hrs. α2, α3, α4, α5 and α7 have all been studied with this technique to determine their contribution to medial habenula nucleus (MHN) and LSG somatic nAChRs with reliable functional block by 24–48 hours. Antisense oligonucleotides were also designed to inhibit the expression of nARIA and ARIA.

These oligos were directed against the translation start site or sequence within the N-terminal domain since the sequences are maximally divergent in this region. To optimize the antisense mediated block, and minimize the confounding contribution of pre-existent nARIA and ARIA, antisense was introduced just prior to the initial surge in expression of these factors during development (≈ED4 for nARIA; ≈ED8 for ARIA). Treatment of preganglionic tissue of these ages with the antisense oligos effectively knocked out the expression of these factors and allowed us to ascertain the extent to which each of these factors contributed to developmental changes in nAChR expression.

A question remains as to whether ARIA or nARIA is required for regulation of nAChR channels by presynaptic input. This idea is tested by the selective block of nARIA or ARIA synthesis by antisense-mediated deletion. To optimize the antisense treatment, the region containing the presynaptic neurons is removed prior to the initial surge in nARIA and ARIA expression (E4 and E8, cord; E4 septal region). In this manner we may succeed in blocking the major increase in expression, thereby obviating effects of pre-existent nARIA or ARIA. Presynaptic microexplants are treated for 24–48 hrs in vitro with antisense oligos targeted to the initiation region of nARIA or ARIA mRNA. Then, nARIA or ARIA activity may be assayed in co-culture with LSG or MHN neurons (assay of nAChR macroscopic and single channel currents as above). The efficacy of antisense constructs is confirmed by quantitative RT-PCR of control and antisense-treated explants for nARIA, ARIA and transcripts unaltered by the treatment (e.g. actin). Specificity of the antisense is evaluated by assay of oligomers, equivalent in size and composition but with 20–25% mismatched bases. Presynaptic properties (e.g. electrical activity, transmitter release/mini amplitude) may be tested to control for other non-specific effects of the antisense.

Comparison of the Affinity of nARIA vs ARIA for Heparin Sulfate Proteoglycan

MCF7 breast tumor cells were treated with conditioned media from either ARIA or nARIA transiently transfected COS1 cells. Some of the media was prebound with heparin attached to glass beads. Prior to treatment, the beads were pelleted by centrifugation to remove any heparin associated proteins.

The supernatant was used to treat the MCF7 cells and tyrosine phosphorylation of the ARIA/nARIA receptor was analyzed. See FIG. 15. It appears that the ARIA is binding to heparin and is removed from the media by centrifugation. The nARIA lane shows a slight drop in signal which is unaffected by increasing concentrations of heparin (from 6 $\mu$g–60 $\mu$g) It is possible that this slight drop is an artifact of differential binding between the lanes and thus nARIA does not bind heparin.

Heparin is a component of both the cellular surface and the extracellular matrix. The difference in the binding affinities of nARIA and ARIA for heparin have two implications. (1) Heparin can affect the affinity of the ligand for the receptor as has been previously shown for HB-EGF. In this case, heparin may increase the affinity for the receptor. Accordingly, a given amount of ARIA may have higher affinity and thus more cellular activity and effect than the equivalent amount of nARIA. This implication may extend to other possible effects of the physiological concentration of the ligand. (2) The lack of affinity for heparin may result in greater solubility of nARIA in vivo since the molecule will not be bound to the extracellular heparin. This possibility may influence the localization of the ligand effects and the point concentration of the ligand.

Conclusions

The series of experiments described herein are some examples illustrating possible uses of nARIA. As discussed above herein, there are many other possible therapeutic, diagnostic and pharmacologic uses of nARIA. The biological role of nARIA has been shown to be distinct from that of ARIA and from other members of the heregulin/NDF family.

Therefore, nARIA may be useful in therapeutic treatments and as a diagnostic tool for abnormal neuronal conditions. In addition, a comparison of the expression levels and activities of the members of the NDF/heregulin/ARIA family may prove to be useful in the characterization and treatment of neuronal disorders and abnormal conditions and neurological developmental questions which are at this time unanswered.

EXAMPLE 4

The n-ARIA Isoform of Neuregulin is both Necessary and Sufficient for the Induction of Acetylcholine-receptors in Neurons.

It is clear that the n-ARIA isoform of neuregulin is both necessary and sufficient for the induction of acetylcholine-receptors (nAChR) in neurons. The induction of nAChR expression normally occurs at specific sites within the CNS and PNS during synapse formation and can be mimicked by presynaptic input or presynaptic-input conditioned media. Definitive evidence has been uncovered showing that the activity of presynaptic input in inducing receptor expression is mediated by n-ARIA. The timing and pattern of expression as well as the primary structure and functional effects of n-ARIA differ importantly from the other neuregulins.

The Expression Profile of n-ARIA is Distinct from that of the Ig-domain Containing Forms The n-ARIA sequence is unique. An extracellular Ig-like motif, common to all other neuregulins, is replaced by a highly conserved cys rich domain (98% identical chick to human) and linked to a $\beta$1 type EGF-like domain.

n-ARIA is the only neuregulin isoform for which expression is restricted to the nervous system (both PCR and Northern analyses).

n-ARIA expression, unlike the Ig containing forms, is apparent at the earliest stages of neuronal differentiation (E2–E3 in chick; PCR and Northern analyses).

The development of isoform specific antibodies and the assessment of the distribution of n-ARIA protein in the CNS and PNS has been performed. A polyclonal sheep antibody was raised which is specific to the cysteine rich domain containing isoforms of the "neu"-regulin gene. This antibody was developed against a peptide sequence encoding the hydrophilic portion within the highly conserved domain. The antibody is capable of recognizing both the denatured and natural protein states on solid matrix support (FIG. 16). Immunohistochemical studies demonstrate that this antibody recognizes both avian and mammalian homologues of the nARIA protein. Immunohistochemical studies have also demonstrated that:

Unlike the Ig containing forms, n-ARIA is largely (but not exclusively) expressed by cholinergic and/or cholinoceptive neurons. n-ARIA expression is prominent in medial septal cholinergic nuclei, basal forebrain, deep cerebellar nuclei, cerebellar Purkinje neurons, and retinal ganglion neurons as well as in cranial, somatic and visceral motor nuclei.

n-ARIA protein appears to be targeted to axons and axon terminals as soon as such projections can be detected either in vitro or in vivo. n-ARIA immunoreactivity is localized in motor nerve terminal at the neuromuscular junction and "double" staining indicates that n-ARIA expression aligns with (post synaptic) a bungarotoxin binding, which reveals the distribution of muscle AchRs. n-ARIA immunoreactivity is also detected in axonal terminals and en passant synapses on CNS and PNS neurons (FIG. 17).

The Functional Profile of n-ARIA is Distinct from that of the Ig-domain Containing Forms n-ARIA is more soluble than the Ig-domain containing forms and is unaffected by heparin and less avidly bound by extracellular matrix proteins.

The activity of n-ARIA in inducing tyrosine phosphorylation in neurons is more potent, more rapid and more persistent than Ig-domain containing forms.

Figure 18:
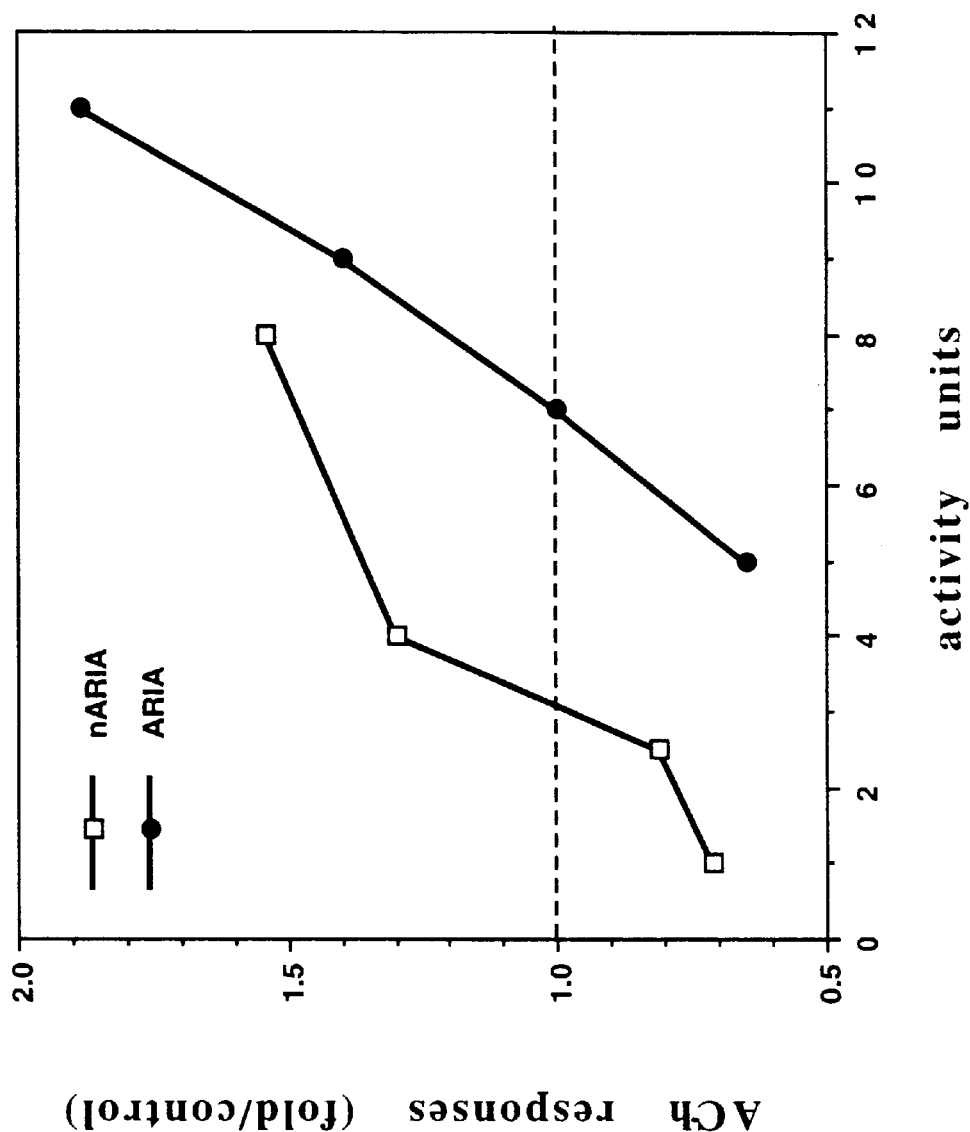

The induction of specific nAChR subunits and the enhancement of nAChR-currents by presynaptic input are specifically mimicked by recombinant n-ARIA protein. The activity of n-ARIA in inducing receptor expression in neurons is more potent and more persistent than Ig-domain containing forms (FIG. 18).

The ability to enhance α3 type nAChR subunit gene expression is unique to the n-ARIA isoform.

Most importantly, the induction of specific nAChR subunits and the enhancement of nAChR-currents by presynaptic input are selectively blocked by prior exposure of the input to n-ARIA specific antisense-oligonucleotides (FIG. 19) or n-ARIA specific antibodies.

The n-ARIA Isoforms

The role of n-ARIA in the differentiation and synaptic function of the septal cholinergic neurons that project to hippocampus and amygdala has been investigated.

Specifically, evidence suggests that n-ARIA might collaborate with other growth factors, previously implicated in the differentiated function and perhaps, survival of CNS cholinergic neurons.

n-ARIA may induce several parameters of differentiated phenotype in central cholinergic neurons. The effects of n-ARIA ±target-derived growth factors, on ACH synthesis and release have been examined. Transient depletion of n-ARIA (in vitro by antisense or antibody treatments to "knock down" endogenous n-ARIA) has been utilized to initially test for n-ARIA dependent changes cholinergic neurons.

Genomic probes to n-ARIA (i.e. the sequence encoding the crucial cys rich domain) have been developed. The effects of an n-ARIA-selective gene knock out was examined by using homologous recombination with subsequent excision of the selectable marker employing the Cre-LOXP approach. The n-ARIA exon-specific knock-outs are expected to survive embryogenesis as, unlike other neuregulins (including ARIA), expression is confined to the nervous system, allowing determination of the role of n-ARIA in the differentiation, synaptic function and survival of CNS cholinergic neurons.

References

Abuchowski et al., In: "Enzymes as Drugs", Holcenberg et al., eds. Wiley-Interscience, New York, N.Y., 367–383 (1981).

Arenella, L. S., Oliva, J. M. Jacob, M. H. (1993) Reduced levels of acetylcholine receptor expression in chick ciliary ganglion neurons developing in the absence of innervation. *J. Neuroscience* 13(10):4525–37.

Ausubel, F., Brent, R., Kingston, R., Moore, D., Seidman, J. G., Smith, J. and Struhl, K. eds. (1994) *Current protocols in Molecular Biology* Green Publishing Associates, Inc.

Berg, D. K., Boyd, R. T., Halvorsen, S. W. Higgins, L. S., Jacob, M. H., Margiotta, J. F. (1989) Regulating the number and function of neuronal acetylcholine receptors. *Trends Neurosci.* 12:16–21.

Bertrand, D., Cooper, S., Valera, D. and Ballivet, M. (1991) Electrophysiology of neuronal nicotinic acetylcholine receptors expressed in Xenopus oocytes following nuclear injection of genes or cDNAs. *Med Neurosci.* 4:174–193.

Betz, H. (1990) Homology and analogy in transmembrane channel design: lessons from synaptic membrane proteins. *Biochemistry* 29:3591–99.

Boulter, J., Evans, K., Goldman, D., Martin, G., Treco., D., Heinemann, S., Patrick, J. (1986) Isolation of a cDNA clone coding for a possible neural nicotinic acetylcholine receptor α-subunit. *Nature* 319:368–74.

Boyd, R. T., Jacob, M. H., Couturier, S., Ballivet, M., Berg, K. D. (1988) Expression and regulation of neuronal acetylcholine receptor nRNA in chick ciliary ganglia. *Neuron* 1:495–502.

Brussaard, A. B., Yang, X., Doyle, J. P., Huck, S., Role. L. W. (1994) Developmental regulation of multiple nicotinic ADhR channel subtypes in embryonic chick habenula neurons: Contributions of both the α2 and α4 subunit genes. *Pflugers Archiv.* (In press.).

Brussaard, A. B., McGehee, D. S. and Role, L. W. (1994b) Presynaptic input, in the absence of target contact, recapitulates a subset of the modifications of nAChR channels induced in vivo to enhance synaptic transmission. (to be submitted to *J. Physiol.*)

Carpenter et al., *Toxicol. Appl. Pharmacol.*, 18:35–40 (1971).

Clarke, P. B. S., Hamill, G. S., Nadi, N. S., Jacobowitz, D. M., Pert, A. (1986) $^3$H-nicotine-and $^{125}$I-alpha-bungarotoxin-labeled nicotinic receptors in the interpeduncular nucleus of rats. II. Effects of habenular deafferentation. *J. Comp. Neur.* 251:407–13.

Conroy, W. G., Vernallis, A. B., Berg, D. K., (1992) The α5 gene product assembles with multiple acetylcholine receptor subunits to form distinctive receptor subtypes in brain. *Neuron* 9:679–91.

Deneris, E. S., Connolly, J., Rogers, S. W., Duviosin, R. (1991) Pharmacological and functional diversity of neuronal nicotinic acetylcholine receptors. *Trends Pharmacol. Sci* 12:34–40.

Devay, P., Qu, X. and Role, L. W. (1994) Developmental regulation of nAChR subunit gene expression during establishment of pre- and post-synaptic connections of lumbar sympathetic neurons of embryonic chicken. *Devel. Biol.* 162:56–70.

Engisch, K. L., Fischbach, G. D. (1994) The development of ACH- and GABA-activated currents in embryonic chick ciliary ganglion neurons in the absence of innervation in vivo. *J. Neurosci.* 1992, 12:1115–25.

Falls, D., Rosen, K., Corfas, G., Lane, W. and Fischbach, G. D (1993) ARIA, a protein that stimulates acetylcholine receptor synthesis, is a member of the Neu ligand family. *Cell* 72:801–815.

Fischbach, G. D., Role, L. W. and Hume, R. I. (1984) The accumulation of acetylcholine receptors at nerve-muscle synapses in culture. In: *Cellular and Molecular Biology of Neuronal Development.* I. Black (ed.), Plenum Press. pp 107–115.

Gardette, R., Listerud, M. D., Brussaard, A. B., Role, L. W. (1991) Developmental changes in transmitter sensitivity and synaptic transmission in embryonic chicken sympathetic neurons innervated in vitro. *Dev. Biol.* 147:83–95.

Grynkiewicz, G., Poenie, M. and Tsien, R. Y. (1985) A new generation of Ca2+ indicators with greatly improved fluorescence properties, *J.Biol. Chem.* 260:3440–3450.

Habecker, B. and Landis, S. (1994) Noradrenergic Regulation of Cholinergic Differentiation. *Science* 264:1602–1604.

Hammil, O. P., Marty, A., Neher, E., Sakemann, B. and Sigworth, F. J. (1981) Improved patch-clamp techniques for high-resolution current recording from cells and cell-free membrane patches. *Pflugers Arch.* 391:85–100.

Hasselmo, M. E. and Bower, J. M. (1993) Acetylcholine and memory. *Trends in Neurosci.* 16:218–222.

Heinemann, S., Boulter, J., Deneris, E., Connoly, J., Duvousin, R., Papke, R., Patrick, J. (1990) The brain nicotinic acetylcholine receptor gene family. *Progr. Brain Res.* 86:195–203.

Holmes, W. E., Sliwkowski, M. X., Akita, R. W., Henzel, W. J., Lee, J., Park, J. W., Yansura, D., Abadi, N., Raab, H., Lewis, G. D., et al. (1992) Identification of heregulin, a specific activator of p185$^{erbB2}$. *Science* 256:1205–1210.

Jacob, M. H. (1991) Acetylcholine receptor expression in developing chick ciliary ganglion neurons. *J. Neurosci.* 11:1701–12.

Katre et al., *Proc. Natl. Acad. Sci. USA* 84:1487–1491 (1987).

Köhler and Milstein *Eur. J. Immunol.* 6:511–519 (1976).

Kriegler, M. (1990) Gene Transfer and Expression: A Laboratory Manual, Stockton Press, New York, N.Y.

Levey, M. S., Brumwell, C., Dryer, S., Jacob, M. (1994) Innervation and target tissue interactions differentially regulate acetylcholine receptor subunit transcript levels in Lipscombe, D., Madison, D. V., Poenie, M., Reuter, H., Tsien, R. W. and Tsien, R. Y. (1988) Imaging of cytosolic Ca2+ transients arising from Ca2+ stores and Ca2+ channels in sympathetic neurons. *Neuron* 1:355–365.

Listerud, M., Brussard, A. B., Devay, P., Colman, D. R., Role, L. W. (1991) Functional contribution of neuronal AChR subunits by antisense oligonucleotides. *Science* 254:1518–21.

Marchionni, M. A., Goodearl, A. D., Chen, M. S., Bermingham, M. O., Kirk, C., Hendricks, M., Danehy, F., Misumi, D., Sudhalter, J., Kobayashi, K., et al., (1993) Glial growth factors are alternatively spliced erbB2 ligands expressed in the nervous system. *Nature* 362:312–318.

Mandelzys, A., Pie, B., Deneris, E. S., Cooper, E. (1994) The developmental increase in ACh current densities on rat sympathetic neurons correlates with changes in nicotinic Ach receptor a-subunit gene expression and occurs independently of innervation. *J. Neurosci.* 15:2357–64.

Margiotta, J. F., Gurantz, D. (1989) Changes in the number, function and regulation of nicotinic acetylcholine receptors during neuronal development. *Dev. Biol.* 135:326–39.

McGehee, D. S., and Role, L. W. (1995) Physiological Diversity of nicotinic acetylcholine receptors expressed by vertebrate neurons. *Annual Review of Physiology* (in press).

McGehee, D. S., Yang, X., Devay, P., Heath, M. J. S., Role, L. W. Nicotine potentiates synaptic transmission through presynaptic aBgTx sensitive acetylcholine receptors. *Soc. Neurosci. Abstr.* 19:463.

Moss, B. L. and Role, L. W. (1993) Enhanced ACh sensitivity is accompanied by changes in ACh receptor channel properties and segregation of ACh receptor subtypes on sympathetic neurons during innervation in vivo. *J. Neurosci.* 13:13–28.

Moss, B. L., Schuetze, S. M., Role. L. W. (1989) Functional properties and developmental regulation of nicotinic acetylcholine receptors on embryonic chicken sympathetic neurons. *Neuron* 3:597–607.

Nef, P., Oneyser, S., Alliod, D., Couturier, S., Ballivet, M. (1988) Genes expressed in the brain define three distinct neuronal nicotinic acetylcholine α3-receptors. *EMBO J.* 7:595–601.

Newmark et al., *J. Appl. Biochem.* 4:185–189 (1982).

Press, W., Flannery, B., Teukolsky, S. and Vettering, W. P. (1986) Are two distributions different? Komolgorov-Smirnov test. In *Numerical Recipes: The Art of Scientific Computing* (New York: Cambridge Univ. Press) pp 472–475.

Ramirez-Latorre, J., Qu, Z., and Role, L. W. (1993) Participation of α5 in neuronal nicotinic AChR channels. *Soc. Neurosci. Abstr.* 19:1533.

Role, L. W.(1988) Neural regulation of acetylcholine sensitivity of embryonic sympathetic neurons. *Proc. Natl. Acad. Sci. USA* 85:2825–2829.

Role, L. W. (1992) Diversity in primary structure and function of neuronal nicotinic acetylcholine receptor channels. *Curr. Opin. Neurobiol.* 2:254–62.

Sambrook, J., Fritsch, E. F. and Maniatis, T. (1989). Molecular cloning: a laboratory manual (Cold Spring Harbor Laboratory Press, Cold Spring Harbor, N.Y.), 2nd Ed.

Sargent, P. B. (1993) The diversity of neuronal nicotinic acetylcholine receptors. *Ann Rev. Neurosci.* 16:403–33.

Seguela, P., Wadiche, J., Dineley-Miller, K., Dani, J. A., Patrick, J. W., (1993) Molecular cloning, functional properties and distribution of rat brain α7: a nicotinic cation channel highly permeable to calcium. *J. Neurosci.* 13:596–604.

Sendecor and Cochran, (1989)

Simmons, L. K., Moss, B. L., Schuetze, S. M. and Role, L. W. (1988) Developmental regulation and modulation of neuronal nicotinic acetylcholine receptor channels in *Nicotinic Acetylcholine Receptors in the Nervous System.* NATO ASI series H: Cell Biology. Vol. 25H, Ed. F. Clementi, C. Gotti & E Sher, Springer-Verlag, Berlin-Heidelberg, pp 379–392.

Smith, M. A., Margiotta, J. F., Berg, D. K. (1983) Differential regulation of acetylcholine sensitivity and α-bungarotoxin-binding sites on ciliary ganglion neurons in cell culture. *J. Neurosci.* 7:149–70.

Tsien, R. Y. (1989) Fluorescent probes of cell signalling. *Ann. Rev. Neurosci.* 12:227–253.

Vernallis, A. B., Conroy, W. g., Berg, D. K. (1993) Neurons assemble acetylcholine receptors with as many as three kinds of subunits while maintaining subunit segregation among receptor subtypes. *Neuron.* 10:451–64.

Wada, E., Wada, K., Boulter, J., Deneris, E., Heinemann, S., Patrick, J., Swanson, L. W. (1989) Distribution of α2, α3, α4, and β2 neuronal nicotinic receptor subunit mRNAs in the central nervous system: a hybridization histochemical study in the rat. *J. Comp. Neurol.* 284:314:35.

Wen, D., Peles, E., Cupples, R., Suggs, S. V., Bacus, S. S., Luo, Y., Trail, G., Hu, S. Silbiger, S. M., Ben Levy, R. et al., (1992). New differentiation factor: a transmembrane glycoprotein containing an EGF domain and an immunoglobulin homology unit. *Cell* 69:559–572.

Wen, D., Suggs, S. V., Karunagaran, D., Liu, N., Cupples, R. L., Luo, Y., Janssen, A. M., Ben-Baruch, N., Trollinger, D. B., Jacobsen, V. L., Meng, S. -Y., Lu, H. S., Hu, S., Chang, D., Yang, W., Yanigahara, D., Koski, R. A., and Yarden, Y. (1994) *Mol. Cell. Biol.* 14:1909–1919.

What is claimed is:

1. An isolated nucleic acid molecule encoding an nARIA polypeptide, said nucleic acid molecule having the sequence shown from base 93 to base 758 of FIG. 3 (SEQ ID NO: 3) or having a sequence which is at least 75% identical with the sequence shown from base 93 to base 758 of FIG. 3 (SEQ ID NO: 3), wherein the nARIA polypeptide increases the number of functional acetylcholine receptors in neurons in response to acetylcholine.

2. The nucleic acid of claim 1, wherein the nucleic acid encodes human nARIA.

3. The nucleic acid of claim 2, wherein the nucleic acid comprises the sequence shown from base 93 to base 758 of FIG. 3 (SEO ID NO:3).

4. The nucleic acid of claim 1, wherein the nucleic acid is DNA, cDNA or RNA.

5. A replicable vector comprising the nucleic acid of claim 1.

6. The replicable vector of claim 5, wherein the vector is a prokaryotic expression vector, a yeast expression vector, a baculovirus expression vector, a mammalian expression vector, an episomal mammalian expression vector, pKK233-2, pEUK-C1, pREP4, pBlueBacHis A, pYES2, pSE280 or pEBVHis.

7. A host cell comprising the vector of claim 6.

8. The host cell of claim 7, wherein the host cell is a eukaryotic cell, a somatic cell, a germ cell, a neuronal cell, a myocyte, a prokaryotic cell, a virus packaging cell, or a stem cell.

9. The nucleic acid molecule of claim 1, wherein the nucleic acid is labeled with a detectable moiety.

10. The nucleic acid of claim 9, wherein the detectable moiety is a fluorescent label, a digoxigenin, a biotin, an enzyme, a radioactive atom, a paramagnetic ion, and a chemiluminescent label.

11. The nucleic acid molecule of claim 1, wherein the nARIA polypeptide has at least 85% amino acid sequence identity with the sequence shown in FIG. 4 (SEQ ID NO: 4).

12. The nucleic acid molecule of claim 1, wherein the nARIA polypeptide has at least 90% amino acid sequence identity with the sequence shown in FIG. 4 (SEQ ID NO: 4).

13. The nucleic acid molecule of claim 1, wherein the nARIA polypeptide has at least 95% amino acid sequence identity with the sequence shown in FIG. 4 (SEQ ID NO: 4).

14. An isolated nucleic acid molecule comprising a unique nARIA sequence in a 3' to 5' orientation, antisense to at least a portion of a nucleic acid molecule encoding nARIA polypeptide, said nucleic acid molecule encoding nARIA polypetide having the sequence shown from base 93 to base 758 of FIG. 3 (SEQ ID NO: 3) or having a sequence which is at least 75% identical with the sequence shown from base 93 to base 758 of FIG. 3 (SEQ ID NO: 3), wherein the nARIA potypeptide increases the number of functional acetylcholine receptors in neurons in response to acetylcholine.

15. The nucleic acid of claim 14, wherein the molecule is antisense to a unique sequence within the sequence shown from base 93 to base 758 of FIG. 3 (SEO ID NO:3).

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear (xi) SEQUENCE DESCRIPTION: SEQ ID NO:1:

```
CGGATGCTGC TGCTACTGTC ACTTCTGCCG CTGCCGCTGT TGTTACAGAT TTTGCTTTTG      60

CTCCTTCTAC CGCATGACAA TTGTTTTCCT CGCCTAAGCA GATACCAGCC TCAGATGCTC     120

AAGGTGAGAG TCTTGCCTTT CGCTCTGGGC TATTGGTTCA CTTAATCCGG TCAATTTGTT     180

CGCTGCTCGT GGTTGTCTTT CTCCCCGCCC TCCTTCCCCC TGTTTTGTTT TGTTTCGCTT     240

GCTTTCGGGG GGACGCTCCT TCCCTCAGTC AGAAGAGCTG GAATTGCTTG AGAGGCGTAT     300

AAGGAATTAT AAAAGTGGCC AGGAAACACG AGCGCAGTGA CTGCAGAGCT GCCCTTGGCT     360

TCGGCAAGGC AGCGTGAGCG GCAGAGGGCT CGGGCAGGGG GCGGGGGGTC TCCTTTTTCC     420

CGTGCGTTCC TCTTCTCCCA GTTCGGATGA TGTTGCTGTT TCGGACCTCT CGCTGACTCC     480

TGCCCTGTGA TTTTTGCTGA GCGCTGTGAC TGTTACTCCG TCTCTTTCTG TCTGTGTTTC     540

ACAGTAATGG ACTGTGATAG AGTTAAGGCC TTTTGGAGGT GAGCTGTGTC ACAGCTGATG     600

CTTAAACATG TCTGAAGTAG GCACCGAGAC TTTCCCCAGC CCCTCGGCTC AGCTGAGCCC     660

TGATGCATCC CTTGGCGGGC TCCCGGCTGA GGAGAACATG CCGGGGCCCC ACAGAGAGGA     720

CAGCAGGGTC CCAGGTGTGG CAGGCCTGGC CTCGACCTGC TGCGTGTGCC TGGAAGCAGA     780

GCGACTGAAG GGCTGCCTCA ACTCTGAGAA GATCTGCATC GCCCCTATCC TGGCTTGCCT     840

GCTCAGCCTC TGCCTCTGCA TTGCTGGCCT CAAGTGGGTC TTTGTGGACA AGATTTTTGA     900

GTATGACTCT CCTACACACC TTGACCCTGG GAGGATAGGA CAAGACCCAA GGAGCACTGT     960

GGATCCTACA GCTCTGTCTG CCTGGGTGCC TTCGGAGGTG TATGCCTCAC CCTTCCCCAT    1020

ACCTAGCCTT GAGAGCAAGG CTGAAGTGAC AGTGCAAACT GACAGCTCGC TCGTGCCCTC    1080

CAGGCCCTTC CTTCAGCCTT CTCTCTACAA CCGCATCCTA GATGTCGGGT TGTGGTCCTC    1140

TGCCACACCG TCACTGTCAC CATCCTCCCT GGAGCCTACC ACGGCATCTC AGGCACAAGC    1200

AACAGAAACC AATCTCCAAA CTGCTCCAAA ACTTTCCACT TCTACATCTA CAACTGGGAC    1260

AAGTCATCTC ACAAAATGTG ACATAAAGCA GAAAGCCTTC TGTGTAAATG GGGAGAGTG     1320

CTACATGGTT AAAGACCTCC CAAACCCTCC ACGATACCTA TGCAGGTGCC CAAATGAATT    1380

TACTGGTGAT CGCTGCCAAA ACTACGTAAT GGCCAGCTTC TACAAGCATC TTGGGATTGA    1440

ATTTATGGAA GCTGAGGAAC TGTACCAGAA ACGGGTGCTG ACCATAACTG GCATTTGCAT    1500

TGCTCTTCTA GTAGTTGGCA TCATGTGTGT GGTGGCCTAC TGCAAAACCA AGAAGCAGAG    1560

GAAAAAGTTG CATGACCGCC TTCGGCAGAG CCTTCGCTCA GAGAGGAACA ACGTTATGAA    1620

CATGGCAAAT GGGCCACACC ACCCCAACCC ACCACCAGAC AATGTCCAGC TGGTGAATCA    1680

GTACGTTTCA AAAAACATAA TCTCCAGTGA ACGTGTCGTT GAGCGAGAAA CCGAGACCTC    1740

GTTTTCCACA AGCCACTACA CCTCAACAAC TCATCACTCC ATGACAGTCA CCCAGACGCC    1800

TAGCCACAGC TGGAGTAATG GCCATACCGA AAGCATTCTC TCCGAAAGCC ACTCCGTGCT    1860
```

-continued

```
CGTCAGCTCC TCAGTGGAGA ATAGCAGGCA CACCAGCCCA ACAGGGCCAC GAGGCCGCCT    1920

CAATGGCATT GGTGGGCCAA GGGAAGGCAA CAGCTTCCTC CGGCATGCAA GAGAGACCCC    1980

TGACTCCTAC CGAGACTCTC CTCACAGTGA AAGGTATGTC TCAGCTATGA CCACACCAGC    2040

TCGCATGTCA CCCGTTGATT TCCACACTCC AACTTCTCCC AAGTCCCCTC CATCTGAAAT    2100

GTCACCACCA GTTTCCAGCT TGACCATCTC CATCCCTTCG GTGGCGGTGA GTCCCTTTAT    2160

GGACGAGGAG AGACCGCTGC TGTTGGTGAC CCCACCACGG CTGCGTGAGA AGTACGACAA    2220

CCACCTTCAG CAATTCAACT CCTTCCACAA CAATCCCACC CATGAGAGCA ACAGTCTGCC    2280

ACCCAGTCCT CTGAGGATAG TGGAGGATGA AGAGTATGAG ACCACGCAGG AGTACGAACC    2340

AGCACAGGAG CCTCCAAAGA AACTCACCAA CAGCCGGAGG GTGAAAAGAA CAAAGCCCAA    2400

TGGCCATATT TCCAGCAGGG TAGAAGTGGA CTCCGACACA AGCTCTCAGA GCACTAGCTC    2460

TGAGAGCGAA ACAGAAGATG AAAGAATAGG TGAGGATACA CCATTTCTTA GCATACAAAA    2520

TCCCATGGCA ACCAGTCTGG AGCCAGCCGC TGCATATCGG CTGGCTGAGA ACAGGACTAA    2580

CCCGGCAAAT CGCTTCTCCA CACCAGAAGA GTTGCAAGCA AGGTTGTCCA GTGTAATAGC    2640

TAACCAAGAC CCTATTGCTG TATAAGACAT AAACAAAACA CATAGATTCA CATGTAAAAC    2700

TTTATTTTAT ATAATGAAGT ATTCCACCTT TAAATTAAAC AATTTATTTT ATTTTAGCAA    2760

TTCCGCTGAT AGAAACAAG AGTGGAAAAA GAAACTTTTA TAAATTAAGT ATACGTATGT    2820

ACAAATGTGT TATGTGCCAT ATGTAGCAAT TTTTTACAGT ATTTCCAAAA TGGGGAAAGA    2880

TATCAATGGT GCCTTTATGT TATGTTATGT TGAGAGCAAG TTTTGTACAG CTACAATGAT    2940

TGCTGTCCCG TAGTATTTTG CAAAACCTTC TAGCCCTCAG TTGTTCTGGC TTTTTTGTGC    3000

ATTGCATTAT AATGACTGGA TGTATGATTT GCAAGAATTG CAGAAGTCCC CATTTGCTTG    3060

TTGTGGAATC CCCAGATCAA AAAGCCCTGT TATGGCACTC ACACCCTATC CACTTCACCA    3120

GGAAAAAAAA AAAATCAAAA AAAAAAAAAA AAAAAAAGA AAAGAAAGAG AAAAAAGAAA    3180

AGAAAAAGAA AAAAAAAGCT GAAAAAATAA AA                                  3212
```

(2) INFORMATION FOR SEQ ID NO:2:

(i) SEQUENCE CHARACTERISTICS:
        (A) LENGTH: 1070 amino acids
        (B) TYPE: amino acid
        (C) STRANDEDNESS: single
        (D) TOPOLOGY: linear (xi) SEQUENCE DESCRIPTION: SEQ ID NO:2:

```
Gly Cys Cys Cys Tyr Cys His Phe Cys Arg Cys Arg Cys Cys Tyr Arg
1               5                   10                  15

Phe Cys Phe Cys Ser Phe Tyr Arg Met Thr Ile Val Phe Leu Ala Xaa
            20                  25                  30

Ala Asp Thr Ser Leu Arg Cys Ser Arg Xaa Glu Ser Cys Leu Ser Leu
        35                  40                  45

Trp Ala Ile Gly Ser Leu Asn Pro Val Asn Leu Phe Ala Ala Arg Gly
    50                  55                  60

Cys Leu Ser Pro Arg Pro Ser Pro Cys Phe Val Leu Phe Arg Leu
65                  70                  75                  80

Leu Ser Gly Gly Arg Ser Phe Pro Gln Ser Glu Glu Leu Glu Leu Leu
                85                  90                  95

Glu Arg Arg Ile Arg Asn Tyr Lys Ser Gly Gln Glu Thr Arg Ala Gln
            100                 105                 110
```

```
Xaa Leu Gln Ser Cys Pro Trp Leu Arg Gln Gly Ser Val Ser Gly Arg
        115                 120                 125

Gly Leu Gly Gln Gly Ala Gly Gly Leu Leu Phe Pro Val Arg Ser Ser
    130                 135                 140

Ser Pro Ser Ser Asp Asp Val Ala Val Ser Asp Leu Ser Leu Thr Pro
145                 150                 155                 160

Ala Leu Xaa Phe Leu Leu Ser Ala Val Thr Val Thr Pro Ser Leu Ser
                165                 170                 175

Val Cys Val Ser Gln Xaa Trp Thr Val Ile Glu Leu Arg Pro Phe Gly
            180                 185                 190

Gly Glu Leu Cys His Ser Xaa Cys Leu Asn Met Ser Glu Val Gly Thr
        195                 200                 205

Glu Thr Phe Pro Ser Pro Ser Ala Gln Leu Ser Pro Asp Ala Ser Leu
    210                 215                 220

Gly Gly Leu Pro Ala Glu Glu Asn Met Pro Gly Pro His Arg Glu Asp
225                 230                 235                 240

Ser Arg Val Pro Gly Val Ala Gly Leu Ala Ser Thr Cys Cys Val Cys
                245                 250                 255

Leu Glu Ala Glu Arg Leu Lys Gly Cys Leu Asn Ser Glu Lys Ile Cys
            260                 265                 270

Ile Ala Pro Ile Leu Ala Cys Leu Leu Ser Leu Cys Leu Cys Ile Ala
        275                 280                 285

Gly Leu Lys Trp Val Phe Val Asp Lys Ile Phe Glu Tyr Asp Ser Pro
    290                 295                 300

Thr His Leu Asp Pro Gly Arg Ile Gly Gln Asp Pro Arg Ser Thr Val
305                 310                 315                 320

Asp Pro Thr Ala Leu Ser Ala Trp Val Pro Ser Glu Val Tyr Ala Ser
                325                 330                 335

Pro Phe Pro Ile Pro Ser Leu Glu Ser Lys Ala Glu Val Thr Val Gln
            340                 345                 350

Thr Asp Ser Ser Leu Val Pro Ser Arg Pro Phe Leu Gln Pro Ser Leu
        355                 360                 365

Tyr Asn Arg Ile Leu Asp Val Gly Leu Trp Ser Ser Ala Thr Pro Ser
    370                 375                 380

Leu Ser Pro Ser Ser Leu Glu Pro Thr Thr Ala Ser Gln Ala Gln Ala
385                 390                 395                 400

Thr Glu Thr Asn Leu Gln Thr Ala Pro Lys Leu Ser Thr Ser Thr Ser
                405                 410                 415

Thr Thr Gly Thr Ser His Leu Thr Lys Cys Asp Ile Lys Gln Lys Ala
            420                 425                 430

Phe Cys Val Asn Gly Gly Glu Cys Tyr Met Val Lys Asp Leu Pro Asn
        435                 440                 445

Pro Pro Arg Tyr Leu Cys Arg Cys Pro Asn Glu Phe Thr Gly Asp Arg
    450                 455                 460

Cys Gln Asn Tyr Val Met Ala Ser Phe Tyr Lys His Leu Gly Ile Glu
465                 470                 475                 480

Phe Met Glu Ala Glu Glu Leu Tyr Gln Lys Arg Val Leu Thr Ile Thr
                485                 490                 495

Gly Ile Cys Ile Ala Leu Leu Val Val Gly Ile Met Cys Val Val Ala
            500                 505                 510

Tyr Cys Lys Thr Lys Lys Gln Arg Lys Lys Leu His Asp Arg Leu Arg
        515                 520                 525

Gln Ser Leu Arg Ser Glu Arg Asn Asn Val Met Asn Met Ala Asn Gly
```

```
                530                 535                 540
Pro His His Pro Asn Pro Pro Asp Asn Val Gln Leu Val Asn Gln
545                 550                 555                 560

Tyr Val Ser Lys Asn Ile Ile Ser Ser Glu Arg Val Val Glu Arg Glu
                565                 570                 575

Thr Glu Thr Ser Phe Ser Thr Ser His Tyr Thr Ser Thr Thr His His
                580                 585                 590

Ser Met Thr Val Thr Gln Thr Pro Ser His Ser Trp Ser Asn Gly His
            595                 600                 605

Thr Glu Ser Ile Leu Ser Glu Ser His Ser Val Leu Val Ser Ser Ser
            610                 615                 620

Val Glu Asn Ser Arg His Thr Ser Pro Thr Gly Pro Arg Gly Arg Leu
625                 630                 635                 640

Asn Gly Ile Gly Gly Pro Arg Glu Gly Asn Ser Phe Leu Arg His Ala
                645                 650                 655

Arg Glu Thr Pro Asp Ser Tyr Arg Asp Ser Pro His Ser Glu Arg Tyr
                660                 665                 670

Val Ser Ala Met Thr Thr Pro Ala Arg Met Ser Pro Val Asp Phe His
            675                 680                 685

Thr Pro Thr Ser Pro Lys Ser Pro Pro Ser Glu Met Ser Pro Pro Val
        690                 695                 700

Ser Ser Leu Thr Ile Ser Ile Pro Ser Val Ala Val Ser Pro Phe Met
705                 710                 715                 720

Asp Glu Glu Arg Pro Leu Leu Leu Val Thr Pro Pro Arg Leu Arg Glu
                725                 730                 735

Lys Tyr Asp Asn His Leu Gln Gln Phe Asn Ser Phe His Asn Asn Pro
                740                 745                 750

Thr His Glu Ser Asn Ser Leu Pro Pro Ser Pro Leu Arg Ile Val Glu
            755                 760                 765

Asp Glu Glu Tyr Glu Thr Thr Gln Glu Tyr Glu Pro Ala Gln Glu Pro
770                 775                 780

Pro Lys Lys Leu Thr Asn Ser Arg Arg Val Lys Arg Thr Lys Pro Asn
785                 790                 795                 800

Gly His Ile Ser Ser Arg Val Glu Val Asp Ser Asp Thr Ser Ser Gln
                805                 810                 815

Ser Thr Ser Ser Glu Ser Glu Thr Glu Asp Glu Arg Ile Gly Glu Asp
            820                 825                 830

Thr Pro Phe Leu Ser Ile Gln Asn Pro Met Ala Thr Ser Leu Glu Pro
        835                 840                 845

Ala Ala Ala Tyr Arg Leu Ala Glu Asn Arg Thr Asn Pro Ala Asn Arg
    850                 855                 860

Phe Ser Thr Pro Glu Glu Leu Gln Ala Arg Leu Ser Ser Val Ile Ala
865                 870                 875                 880

Asn Gln Asp Pro Ile Ala Val Xaa Asp Ile Asn Lys Thr His Arg Phe
                885                 890                 895

Thr Cys Lys Thr Leu Phe Tyr Ile Met Lys Tyr Ser Thr Phe Lys Leu
                900                 905                 910

Asn Asn Leu Phe Tyr Phe Ser Asn Ser Ala Asp Arg Lys Gln Glu Trp
            915                 920                 925

Lys Lys Lys Leu Leu Xaa Ile Lys Tyr Thr Tyr Val Gln Met Cys Tyr
        930                 935                 940

Val Pro Tyr Val Ala Ile Phe Tyr Ser Ile Ser Lys Met Gly Lys Asp
945                 950                 955                 960
```

```
Ile Asn Gly Ala Phe Met Leu Cys Tyr Val Glu Ser Lys Phe Cys Thr
            965                 970                 975
Ala Thr Met Ile Ala Val Pro Xaa Tyr Phe Ala Lys Pro Ser Ser Pro
            980                 985                 990
Gln Leu Phe Trp Leu Phe Cys Ala Leu His Tyr Asn Asp Trp Met Tyr
            995                 1000                1005
Asp Leu Gln Glu Leu Gln Lys Ser Pro Phe Ala Cys Cys Gly Ile Pro
        1010                1015                1020
Arg Ser Lys Ser Pro Val Met Ala Leu Thr Pro Tyr Pro Leu His Gln
1025                1030                1035                1040
Glu Lys Lys Lys Ile Lys Lys Lys Lys Lys Arg Lys Glu Arg
            1045                1050                1055
Glu Lys Arg Lys Glu Lys Glu Lys Lys Ser Xaa Lys Asn Lys
        1060                1065                1070

(2) INFORMATION FOR SEQ ID NO:3:

(i) SEQUENCE CHARACTERISTICS:
        (A) LENGTH: 1351 base pairs
        (B) TYPE: nucleic acid
        (C) STRANDEDNESS: single
        (D) TOPOLOGY: linear (xi) SEQUENCE DESCRIPTION: SEQ ID NO:3:
```

| | | | | | |
|---|---|---|---|---|---|
| CGGCCTGTAA | GATGCTGTAT | CATTTGGTTG | GGGGGGCCTC | TGCGTGGTAA | TGGACCGTGA | 60 |
| GAGCGGCCAG | GCCTTCTTCT | GGAGGTGAGC | CGATGGAGAT | TTATTCCCCA | GACATGTCTG | 120 |
| AGGTCGCCGC | CGAGAGGTCC | TCCAGCCCCT | CCACTCAGCT | GAGTGCAGAC | CCATCTCTTG | 180 |
| ATGGGCTTCC | GGCAGCAGAA | GACATGCCAG | AGCCCCAGAC | TGAAGATGGG | AGAACCCCTG | 240 |
| GACTCGTGGG | CCTGGCCGTG | CCCTGCTGTG | CGTGCCTAGA | AGCTGAGCGC | CTGAGAGGTT | 300 |
| GCCTCAACTC | AGAGAAAATC | TGCATTGTCC | CCATCCTGGC | TTGCCTGGTC | AGCCTCTGCC | 360 |
| TCTGCATCGC | CGGCCTCAAG | TGGGTATTTG | TGGACAAGAT | CTTTGAATAT | GACTCTCCTA | 420 |
| CTCACCTTGA | CCCTGGGGGG | TTAGGCCAGG | ACCCTATTAT | TTCTCTGGAC | GCAACTGCTG | 480 |
| CCTCAGCTGT | GTGGGTGTCG | TCTGAGGCAT | ACACTTCACC | TGTCTCTAGG | GCTCAATCTG | 540 |
| AAAGTGAGGT | TCAAGTTACA | GTGCAAGGTG | ACAAGGCTGT | TGTCTCCTTT | GAACCATCAG | 600 |
| CGGCACCGAC | ACCGAAGAAT | CGTATTTTTG | CCTTTTCTTT | CTTGCCGTCC | ACTGCGCCAT | 660 |
| CCTTCCCTTC | ACCCACCCGG | AACCCTGAGG | TGAGAACGCC | CAAGTCAGCA | ACTCAGCCAC | 720 |
| AAACAACAGA | AACTAATCTC | CAAACTGCTC | CTAAACTTTC | TACATCTACA | TCCACCACTG | 780 |
| GGACAAGCCA | TCTTGTAAAA | TGTGCGGAGA | AGGAGAAAAC | TTTCTGTGTG | AATGGAGGGG | 840 |
| AGTGCTTCAT | GGTGAAAGAC | CTTTCAAACC | CCTCGAGATA | CTTGTGCAAA | GGCGGAGGAG | 900 |
| CTGTACCAGA | AGAGAGTGCT | GACCATAACC | GGCATCTGCA | TCGCCCTCCT | TGTGGTCGGC | 960 |
| ATCATGTGTG | TGGTGGCCTA | CTGCAAAACC | AAGAAACAGC | GGAAAAAGCT | GCATGACCGT | 1020 |
| CTTCGGCAGA | GCCTTCGGTC | TGAACGAAAC | AATACGATGA | ACATTGCCAA | TGGGCCTCAC | 1080 |
| CATCCTAACC | CACCCCCCGA | GAATGTCCAG | CTGGTGAATC | AATACGTATC | TAAAAACGTC | 1140 |
| ATCTCCAGTG | AGCATATTGT | TGAGAGAGAA | GCAGAGACAT | CCTTTTCCAC | CAGTCACTAT | 1200 |
| ACTTCCACAG | CCCATCACTC | CACTACTGTC | ACCCAGACTC | CTAGCCACAG | CTGGAGCAAC | 1260 |
| GGACACACTG | AAAGCATCCT | TTCCGAAAGC | CACTCTGTAA | TCGTGATGTC | ATCCGTAGAA | 1320 |
| AACAGTAGGC | ACAGCAGCCC | AACTGGGGCC | G | | | 1351 |

(2) INFORMATION FOR SEQ ID NO:4:

(i) SEQUENCE CHARACTERISTICS:
        (A) LENGTH: 449 amino acids
        (B) TYPE: amino acid
        (C) STRANDEDNESS: single
        (D) TOPOLOGY: linear (xi) SEQUENCE DESCRIPTION: SEQ ID NO:4:

```
Ala Cys Lys Met Leu Tyr His Leu Val Gly Gly Ala Ser Ala Trp Xaa
1               5                   10                  15

Trp Thr Val Arg Ala Ala Arg Pro Ser Gly Gly Glu Pro Met Glu
                20                  25                  30

Ile Tyr Ser Pro Asp Met Ser Glu Val Ala Ala Glu Arg Ser Ser Ser
                35                  40                  45

Pro Ser Thr Gln Leu Ser Ala Asp Pro Ser Leu Asp Gly Leu Pro Ala
    50                  55                  60

Ala Glu Asp Met Pro Glu Pro Gln Thr Glu Asp Gly Arg Thr Pro Gly
65                  70                  75                  80

Leu Val Gly Leu Ala Val Pro Cys Cys Ala Cys Leu Glu Ala Glu Arg
                85                  90                  95

Leu Arg Gly Cys Leu Asn Ser Glu Lys Ile Cys Ile Val Pro Ile Leu
                100                 105                 110

Ala Cys Leu Val Ser Leu Cys Leu Cys Ile Ala Gly Leu Lys Trp Val
                115                 120                 125

Phe Val Asp Lys Ile Phe Glu Tyr Asp Ser Pro Thr His Leu Asp Pro
    130                 135                 140

Gly Gly Leu Gly Gln Asp Pro Ile Ile Ser Leu Asp Ala Thr Ala Ala
145                 150                 155                 160

Ser Ala Val Trp Val Ser Ser Glu Ala Tyr Thr Ser Pro Val Ser Arg
                165                 170                 175

Ala Gln Ser Glu Ser Glu Val Gln Val Thr Val Gln Gly Asp Lys Ala
                180                 185                 190

Val Val Ser Phe Glu Pro Ser Ala Ala Pro Thr Pro Lys Asn Arg Ile
                195                 200                 205

Phe Ala Phe Ser Phe Leu Pro Ser Thr Ala Pro Ser Phe Pro Ser Pro
    210                 215                 220

Thr Arg Asn Pro Glu Val Arg Thr Pro Lys Ser Ala Thr Gln Pro Gln
225                 230                 235                 240

Thr Thr Glu Thr Asn Leu Gln Thr Ala Pro Lys Leu Ser Thr Ser Thr
                245                 250                 255

Ser Thr Thr Gly Thr Ser His Leu Val Lys Cys Ala Glu Lys Glu Lys
                260                 265                 270

Thr Phe Cys Val Asn Gly Gly Glu Cys Phe Met Val Lys Asp Leu Ser
    275                 280                 285

Asn Pro Ser Arg Tyr Leu Cys Lys Gly Gly Gly Ala Val Pro Glu Glu
    290                 295                 300

Ser Ala Asp His Asn Arg His Leu His Arg Pro Cys Gly Arg His
305                 310                 315                 320

His Val Cys Gly Gly Leu Leu Gln Asn Gln Glu Thr Ala Glu Lys Ala
                325                 330                 335

Ala Xaa Pro Ser Ser Ala Glu Pro Ser Val Xaa Thr Lys Gln Tyr Asp
    340                 345                 350

Glu His Cys Gln Trp Ala Ser Pro Ser Xaa Pro Thr Pro Arg Glu Cys
    355                 360                 365
```

-continued

```
Pro Ala Gly Glu Ser Ile Arg Ile Xaa Lys Arg His Leu Gln Xaa Ala
        370                 375                 380

Tyr Cys Xaa Glu Arg Ser Arg Asp Ile Leu Phe His Gln Ser Leu Tyr
385                     390                 395                 400

Phe His Ser Pro Ser Leu His Tyr Cys His Pro Asp Ser Xaa Pro Gln
                405                 410                 415

Leu Glu Gln Arg Thr His Xaa Lys His Pro Phe Arg Lys Pro Leu Cys
            420                 425                 430

Asn Arg Asp Val Ile Arg Arg Lys Gln Xaa Ala Gln Gln Pro Asn Trp
        435                 440                 445

Gly
```